(12) United States Patent
Hernández Herrero et al.

(10) Patent No.: US 11,591,280 B2
(45) Date of Patent: Feb. 28, 2023

(54) PROCESS AND INTERMEDIATES FOR THE PREPARATION OF ELDECALCITOL

(71) Applicant: FAES FARMA, S.A., Vizcaya (ES)

(72) Inventors: Gonzalo Hernández Herrero, Vizcaya (ES); Neftalí García Domínguez, Vizcaya (ES); Tatiana María Suárez Cortés, Vizcaya (ES); Tania González García, Vizcaya (ES); Generosa Gómez Pácios, Vigo (ES); Yagamare Fall Diop, Vigo (ES); Hugo Santalla García, Vigo (ES); Fátima Garrido Fernández, Vigo (ES)

(73) Assignee: FAES FARMA, S.A.

( * ) Notice: Subject to any disclaimer, the term of this patent is extended or adjusted under 35 U.S.C. 154(b) by 15 days.

(21) Appl. No.: 17/606,807

(22) PCT Filed: May 12, 2020

(86) PCT No.: PCT/EP2020/063196
§ 371 (c)(1),
(2) Date: Oct. 27, 2021

(87) PCT Pub. No.: WO2020/229470
PCT Pub. Date: Nov. 19, 2020

(65) Prior Publication Data
US 2022/0204433 A1  Jun. 30, 2022

(30) Foreign Application Priority Data
May 13, 2019 (EP) .................................. 19382376

(51) Int. Cl.
C07C 41/48 (2006.01)
C07C 43/188 (2006.01)
C07F 7/18 (2006.01)
C07C 401/00 (2006.01)

(52) U.S. Cl.
CPC ............ *C07C 41/48* (2013.01); *C07C 43/188* (2013.01); *C07C 401/00* (2013.01); *C07F 7/1804* (2013.01); *C07F 7/188* (2013.01); *C07F 7/1892* (2013.01); *C07C 2601/14* (2017.05); *C07C 2602/08* (2017.05)

(58) Field of Classification Search
CPC .................. C07C 41/48; C07C 401/00; C07C 2601/14; C07C 2602/08; C07F 7/1804; C07F 7/188; C07F 7/1892
See application file for complete search history.

(56) References Cited

FOREIGN PATENT DOCUMENTS

| CN | 107245045 A | 10/2017 |
|----|----|----|
| EP | 1061070 A1 | 12/2000 |
| EP | 1072582 A1 | 1/2001 |
| KR | 20180057582 | 5/2018 |
| WO | WO2018093223 | 5/2018 |

OTHER PUBLICATIONS

Hatakeyama et al., Synthesis and preliminary biological evaluation of 20-epi-eldecalcitol [20-epi-1alpha,25-dihydroxy-2beta-(3-hydroxypropoxy)vitamin D3: 20-epi-ED-71], J Steroid Biochem Mol Biol. Jul. 2010;121(1-2):25-8.

Noboru Kubodera et al., Synthesis of All Possible A-ring Diastereomers at the 1- and 3-Positions of 1α,25-Dihydroxy-2β-(3-hydroxypropoxy)vitamin D3 (ED-71) Using C2-Symmetrical Epoxide as a Common Starting Material, Anticancer research—International Journal of Cancer Research and Treatment, vol. 29, No. 9, 2009, 3571-3578.

Ono Y. et al.: Synthesis of putative metabolites of 1 alpha,25-dihydroxy-2beta-(3-hydroxypropoxy)vitamin D(3) (ED-71), Steroids, Elsevier Science, vol. 71, No. 7, 2006, 529-540.

Noboru Kubodera and Susumi Hatakeyama, Synthesis of 1α,25-Dihydroxy-2β-(3-hydroxypropoxy)vitamin D3 (Eldecalcitol) and Related Compounds by the Trost Convergent Methodology, Heterocycles 2009, 79, 145-162.

D. Sawada et al., Synthesis of 2α-and 2β-substituted-14-epi-previtamin D 3 and their genomic activity, Tetrahedron 2010, 66, 5407-5423.

Junji Maeyama et al., Two Convergent Approaches to the Synthesis of 1α,25-Dihydroxy-2β-(3-hydroxypropoxy)vitamin D3 (ED-71) by the Lythgoe and the Trost Coupling Reactions, Heterocycles, vol. 70, No. 1, 2006, pp. 295-307.

*Primary Examiner* — Rosalynd A Keys
(74) *Attorney, Agent, or Firm* — Tristan A. Fuierer; Casimir Jones, S.C.

(57) ABSTRACT

The invention relates to new intermediates in the synthesis of Eldecalcitol and to processes for the preparation of said intermediates and of Eldecalcitol.

20 Claims, No Drawings

PROCESS AND INTERMEDIATES FOR THE PREPARATION OF ELDECALCITOL

CROSS-REFERENCE TO RELATED APPLICATIONS

This application is filed under the provisions of 35 U.S.C. § 371 and claims the priority of International Patent Application No. PCT/EP2020/063196 filed on 12 May 2020 entitled "PROCESS AND INTERMEDIATES FOR THE PREPARATION OF ELDECALCITOL" in the name of Gonzalo HERNÁNDEZ HERRERO, et al., which claims priority to European Patent Application No. 19382376.2, filed on 13 May 2019, both of which are hereby incorporated by reference herein in their entirety.

FIELD OF THE INVENTION

The invention relates to new intermediates in the synthesis of Eldecalcitol and to processes for the preparation of said intermediates and of Eldecalcitol.

BACKGROUND OF THE INVENTION

Eldecalcitol is a vitamin D analog with potent biological effects on bone disease such as osteoporosis.

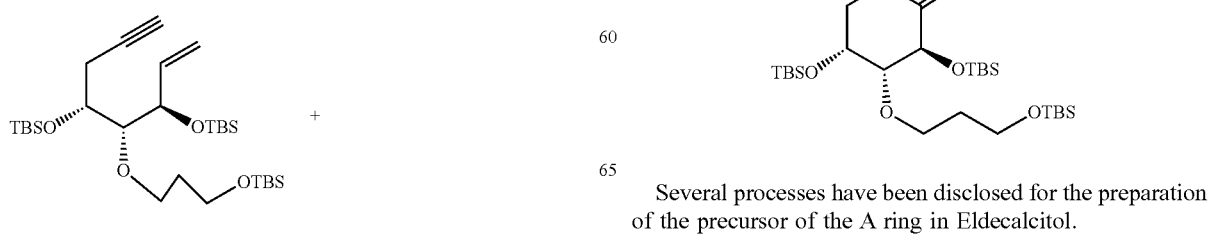

Eldecalcitol

Preparation of Eldecalcitol through Pd catalyzed coupling (Trost coupling reaction) of a precursor of the A ring with a bromo olefin comprising the C/D-ring fragment has been disclosed (Heterocycles 2009, 79, 145-162; Anticancer Research 2009, 29, 3571-3578).

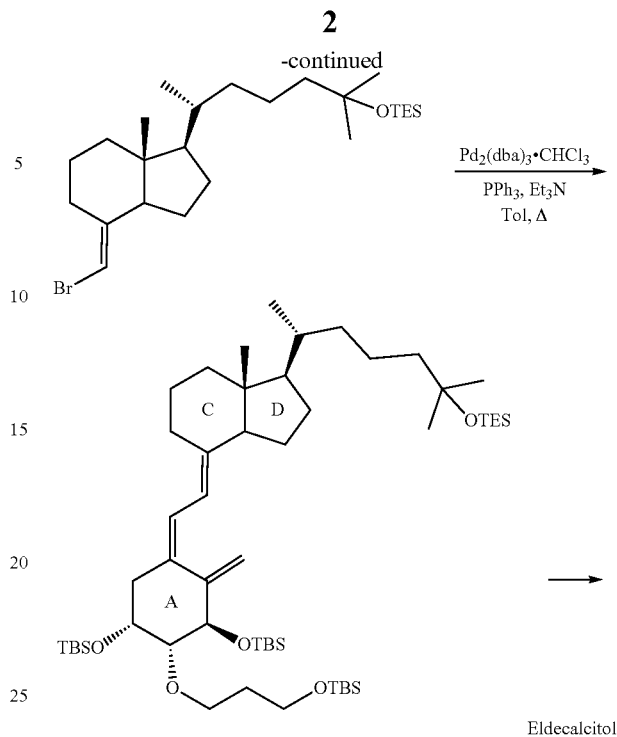

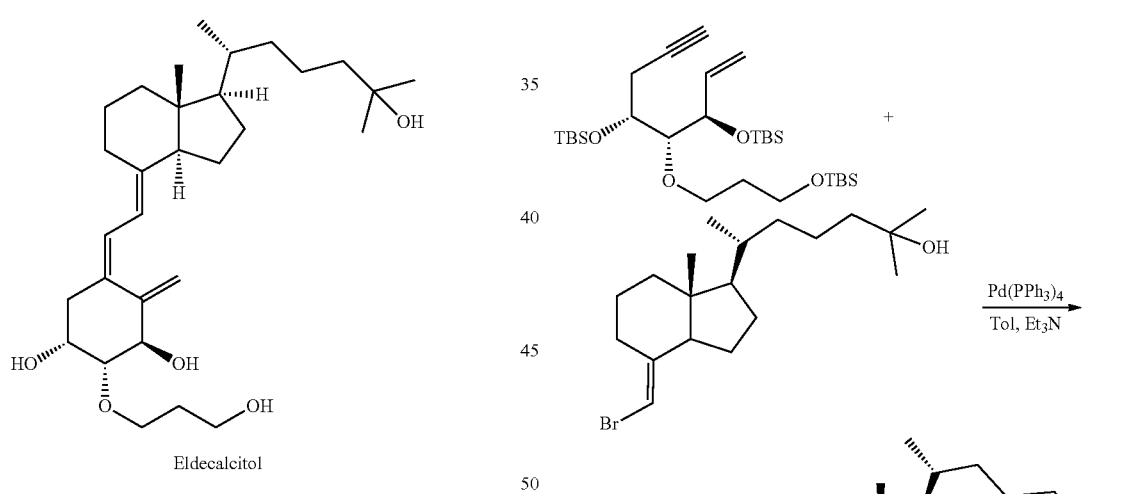

Eldecalcitol

CN 107245045 A also discloses a similar convergent approach for the preparation of Eldecalcitol.

Several processes have been disclosed for the preparation of the precursor of the A ring in Eldecalcitol.

For example, Heterocycles 2009, 79, 145-162 and Anticancer Research 2009, 29, 3571-3578 disclose synthesis of the A ring fragment starting from C2 symmetrical epoxide (8) according to the following route.

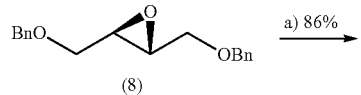

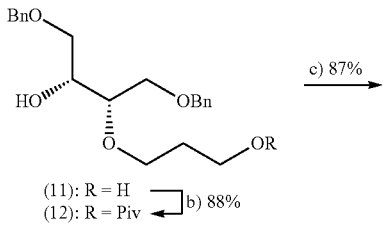

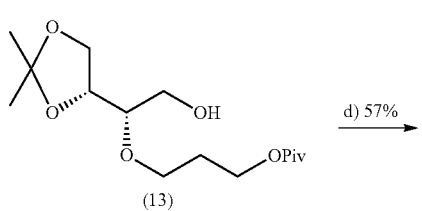

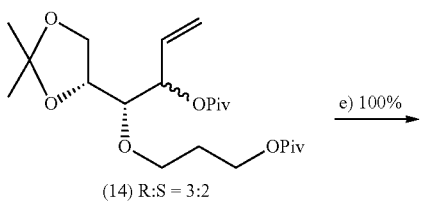

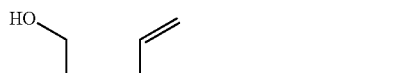

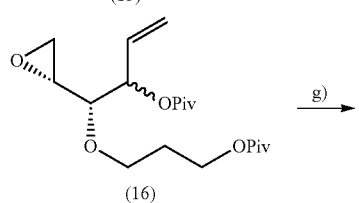

This approach gives rise to a mixture of isomers and so provides the desired compound in a low overall yield. Starting from this same epoxide and following a similar strategy, preparation of A-ring fragment is disclosed in Tetrahedron 2010, 66, 5407-5423. This method also leads to a mixture of isomers and thus to a low yield.

EP 1072582 A1 discloses a process for the preparation of the A ring fragment of Eldecalcitol using D-mannitol as starting material. This route requires many synthetic steps to achieve the desired enyne (18 steps).

All these methods for the preparation of the precursor of the A ring are based on the addition of acetylide to an intermediate epoxide in order to introduce the alkyne moiety. Additionally, due to the length of the synthesis and/or the lack of selectivity, the A ring fragment is obtained in low yields.

It is therefore necessary to develop new processes and intermediates for obtaining Eldecalcitol that overcome all or part of the problems associated with the known processes belonging to the state of the art.

SUMMARY OF THE INVENTION

The invention faces the problem of providing new intermediates for the synthesis of Eldecalcitol, as well as processes for the preparation of said intermediates and of Eldecalcitol.

First, the inventors have developed a new method for the preparation of compounds of formula (I). This method is based on a very different approach over the previous methods in the prior art for related compounds. Additionally, this approach leads to the compounds of formula (I) in a very effective manner, with high yield and purity.

Thus, in a first aspect the invention is directed to a process for preparing a compound of formula (I)

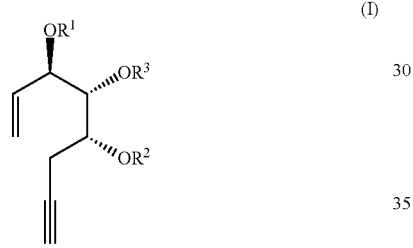

(I)

or a solvate thereof wherein $R^1$, $R^2$ and $R^3$ represent independently a hydroxyl protecting group, wherein $R^3$ is orthogonal to $R^1$ and $R^2$, which comprises:
  (a) oxidative cleavage of the double bond of a compound of formula (II) or a solvate thereof

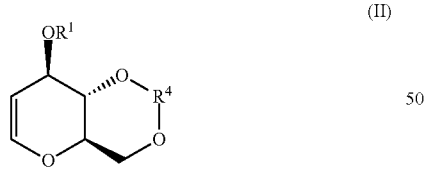

(II)

wherein $R^4$ is a diol protecting group that is orthogonal to $R^1$; to provide a compound of formula (III) or a solvate thereof

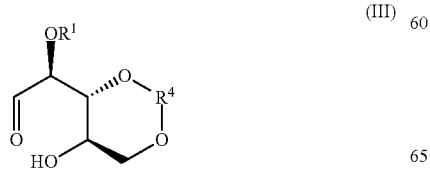

(III)

(b) vinylation of the aldehyde of a compound of formula (III), or a solvate thereof, to provide a compound of formula (IV) or a solvate thereof

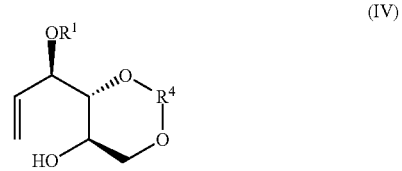

(IV)

(c) protection of the hydroxyl group of a compound of formula (IV), or a solvate thereof, to provide a compound of formula (V) or a solvate thereof

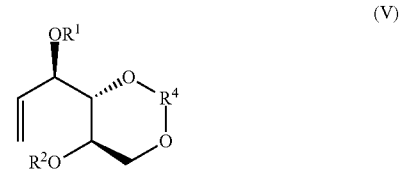

(V)

(d) cleavage of the diol protecting group of a compound of formula (V), or a solvate thereof, to provide a compound of formula (VI) or a solvate thereof

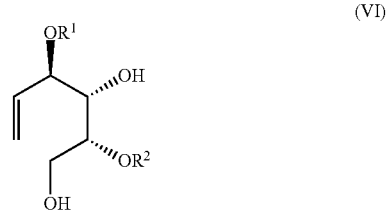

(VI)

(e) conversion of the primary hydroxyl group into the homolog aldehyde and protection of the secondary hydroxyl of a compound of formula (VI), or a solvate thereof, to provide a compound of formula (VII) or a solvate thereof

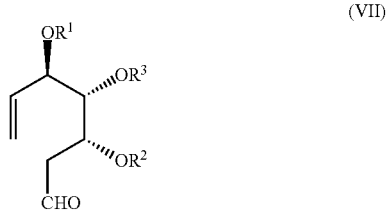

(VII)

and
  (f) Corey-Fuchs reaction of a compound of formula (VII), or a solvate thereof, to provide a compound of formula (I) or a solvate thereof.

The inventors have also found, that compounds of formula (I) can be used in the preparation of Eldecalcitol through a process that comprises introduction of the hydroxypropyl chain at position 2 of A ring at a later stage of the synthesis. Therefore, in a second aspect the invention is directed to a process for preparing Eldecalcitol, or a salt or solvate thereof, wherein the process comprises:

(A) reaction of a compound of formula (I)

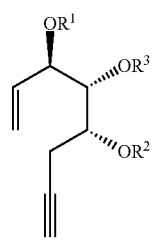

(I)

or a solvate thereof wherein $R^1$, $R^2$ and $R^3$ represent independently a hydroxyl protecting group, wherein $R^3$ is orthogonal to $R^1$ and $R^2$;

with a compound of formula (IX) or with a compound of formula (XXV), or a solvate thereof

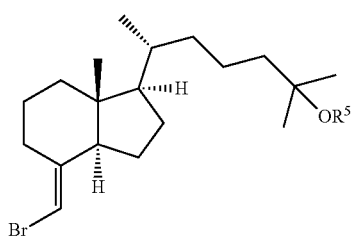

(IX)

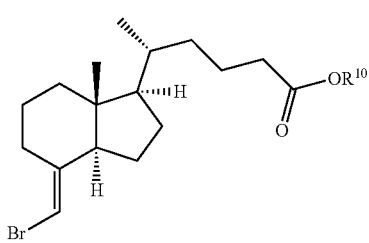

(XXV)

wherein $R^5$ is selected from hydrogen and hydroxyl protecting group, $R^{10}$ is selected from $C_1$-$C_6$ alkyl, $C_6$-$C_{10}$ aryl and ($C_6$-$C_{10}$)aryl($C_1$-$C_6$)alkyl, to provide a compound of formula (X) or a compound of formula (XXVI), respectively, or a solvate thereof

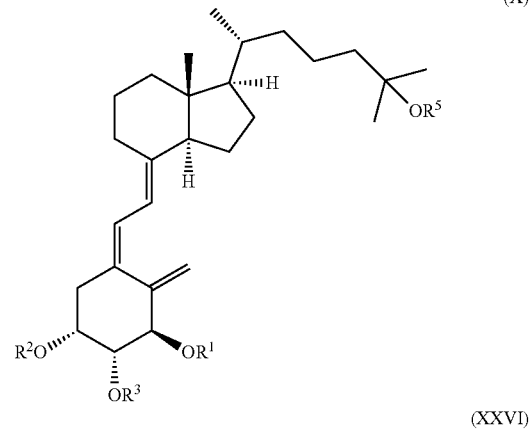

(X)

(XXVI)

(B) when a compound of formula (XXVI) or a solvate thereof is obtained, reaction of a compound of formula (XXVI) with MeLi, and optionally protection of the resulting hydroxyl group, to provide a compound of formula (X) or a solvate thereof, (C) cleavage of the hydroxyl protecting group at position 2 in the compound of formula (X), or a solvate thereof, to provide a compound of formula (XI) or a solvate thereof

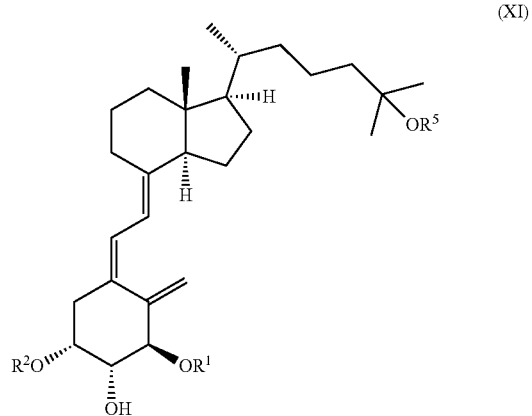

(XI)

(D) reaction of a compound of formula (XI) with a compound of formula (XII) or with a compound of formula (XXII)

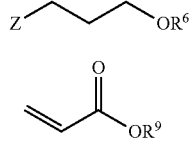
(XII)

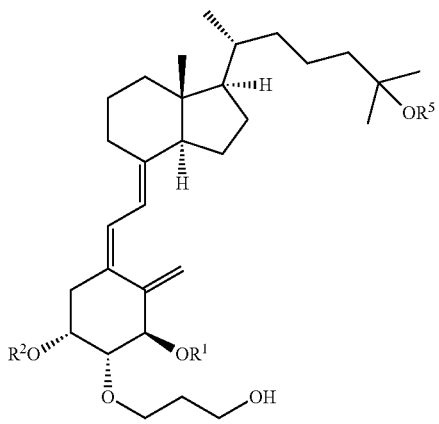
(XXIV)

(XXII)

wherein

Z is a leaving group,

R⁶ is selected from hydrogen and hydroxyl protecting group, and

R⁹ is selected from $C_1$-$C_6$ alkyl, $C_6$-$C_{10}$ aryl and $(C_6$-$C_{10})$aryl$(C_1$-$C_6)$alkyl, to provide a compound of formula (XIII), or a compound of formula (XXIII), or a solvate thereof

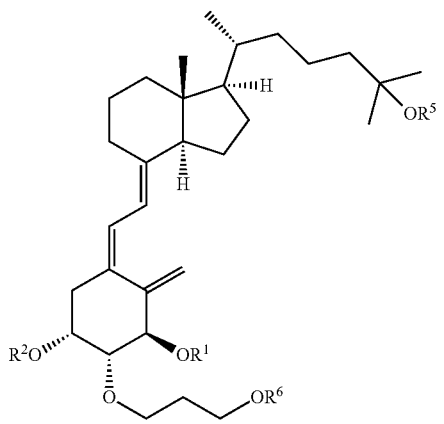
(XIII)

and (F) cleavage of the hydroxyl protecting groups in the compound of formula (XIII), or in the compound of formula (XXIV), or a solvate thereof, to provide Eldecalcitol, or a salt or solvate thereof.

In a third aspect the invention is directed to a compound of formula (I')

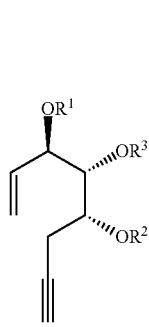
(I')

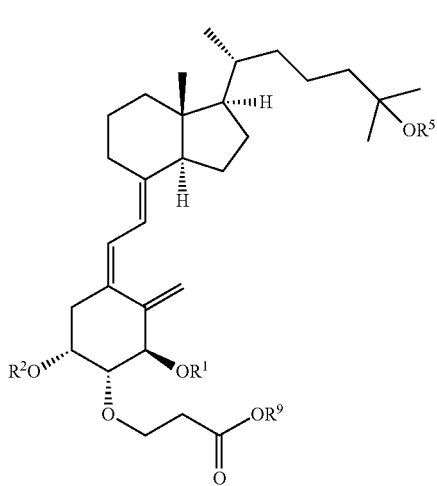
(XXIII)

(E) when a compound of formula (XXIII) or a solvate thereof is obtained, reduction of the ester group of a compound of formula (XXIII), or a solvate thereof, to provide a compound of formula (XXIV) or a solvate thereof or a solvate thereof wherein R¹ and R² represent independently a group selected from:

$C_1$-$C_6$ alkyl, $C_6$-$C_{10}$ aryl, $(C_6$-$C_{10})$aryl$(C_1$-$C_6)$alkyl and $(C_1$-$C_6)$alkoxy$(C_1$-$C_6)$alkyl, —$CH_2$—OR$^a$, wherein R$^a$ is selected $C_1$-$C_6$ alkyl, $C_6$-$C_{10}$ aryl, $(C_6$-$C_{10})$aryl$(C_1$-$C_6)$alkyl and $(C_1$-$C_6)$alkoxy$(C_1$-$C_6)$alkyl, —COR$^b$, wherein R$^b$ is selected from $C_1$-$C_6$ alkyl, $C_6$-$C_{10}$ aryl and $(C_6$-$C_{10})$aryl$(C_1$-$C_6)$alkyl, and —COOR$^c$, wherein R$^c$ is selected from $C_1$-$C_6$ alkyl, $C_6$-$C_{10}$ aryl and $(C_6$-$C_{10})$aryl$(C_1$-$C_6)$alkyl; and R³ is a hydroxyl protecting group orthogonal to R¹ and R².

In a further aspect the invention is directed to a compound of formula (XI)

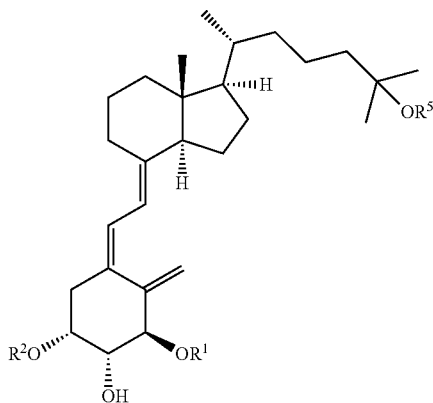

(XI)

or a solvate thereof wherein
$R^1$ and $R^2$ represent independently a hydroxyl protecting group; and
$R^5$ is selected from hydrogen and hydroxyl protecting group.

In another aspect, the invention is directed to a compound of formula (XXIII)

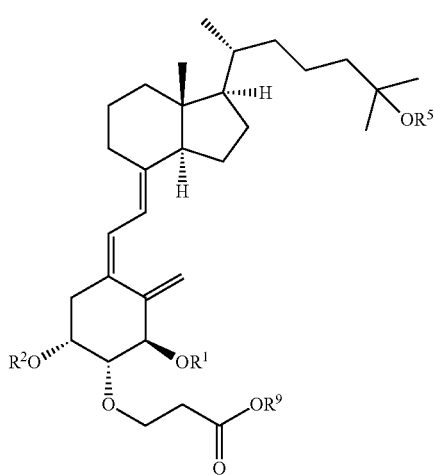

(XXIII)

or a solvate thereof wherein
$R^1$ and $R^2$ represent independently a hydroxyl protecting group;
$R^5$ is selected from hydrogen and hydroxyl protecting group, and
$R^9$ is selected from $C_1$-$C_6$ alkyl, $C_6$-$C_{10}$ aryl and $(C_6$-$C_{10})$aryl$(C_1$-$C_6)$alkyl.

DETAILED DESCRIPTION OF THE INVENTION

The term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, i-propyl, n-butyl, i-butyl, t-butyl, pentyl, hexyl. Preferably, it is methyl or ethyl.

The term "cycloalkyl" refers to a radical derived from cycloalkane containing from 3 to 7 ("$C_3$-$C_7$ cycloalkyl"), preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

The term "aryl" refers to an aromatic group having between 6 and 10 ("$C_6$-$C_{10}$ aryl"), preferably 6 or 10 carbon atoms, comprising 1 or 2 aromatic nuclei fused to one another. Illustrative examples of aryl groups include phenyl, naphthyl, indenyl, phenanthryl, etc. Preferably, it is phenyl.

The term "$(C_6$-$C_{10})$aryl$(C_1$-$C_6)$alkyl" refers to an alkyl group as defined above substituted with an aryl group as defined above. Examples of such groups include benzyl, phenylethyl, phenylpropyl, naphthylmethyl, etc. Preferably, it is benzyl.

The term "alkoxy" designates an alkyl group as defined above, preferably having between 1 and 6 carbon atoms ("$C_1$-$C_6$ alkoxy"), more preferably between 1 and 3 carbon atoms ("$C_1$-$C_3$ alkoxy"), linked to the rest of the molecule through oxygen. Examples of alkoxy include methoxy, ethoxy, i-propoxy, n-propoxy, n-butoxy, s-butoxy t-butoxy, and the like.

The term "aryloxy" designates an aryl group as defined above, preferably having between 6 and 10 carbon atoms ("$C_6$-$C_{10}$ aryloxy"), linked to the rest of the molecule through oxygen. Examples of alkoxy include phenoxy, naphthoxy and diphenoxy.

As used herein, the term "$C_2$-$C_{12}$ alkoxyalkyl" group includes radicals containing a linear or branched alkyl chain interrupted by at least one oxygen atom, preferably by one, two or three, more preferably one or two. The number of carbon atoms indicates the total number of carbon atoms present in the radical. All structural isomers are included. Preferably, the alkoxyalkyl group is a $C_2$-$C_6$ alkoxyalkyl group, more preferably a $C_2$-$C_6$ alkoxyalkyl group, wherein the alkyl chain is interrupted by one or two oxygen atoms.

In a preferred embodiment, the alkoxyalkyl group is a $(C_1$-$C_4)$alkoxy$(C_1$-$C_3)$alkoxy$(C_1$-$C_2)$alkyl group, more preferably a $(C_1$-$C_4)$alkoxy$(C_1$-$C_2)$alkyl group, such as methoxymethyl, ethoxymethyl, tbutoxymethyl and methoxyethoxymethyl.

The term "$(C_6$-$C_{10})$aryloxy$(C_1$-$C_6)$alkyl" refers a radical of the formula $(C_6$-$C_{10})$aryl-O—$(C_1$-$C_6)$alkyl, preferably $(C_6$-$C_{10})$aryl-O—$(C_1$-$C_6)$alkyl, in which the terms "aryl" and "alkyl" have the significance given above. An example of an aryloxyalkyl is phenoxymethyl.

The term "halogen" refers to bromine, chlorine, iodine or fluorine.

The term "heterocyclyl" refers to a saturated or partially unsaturated monocyclic or bicyclic system containing from 3 to 10, preferably 5 to 7, ring atoms containing one or more, specifically one, two, three or four ring heteroatoms independently selected from N, O, and S, and the remaining ring atoms being carbon.

The term "heteroaryl" refers to an aromatic monocyclic or bicyclic system containing from 3 to 10, preferably 5 to 7, ring atoms containing one or more, specifically one, two, three or four ring heteroatoms independently selected from O, N and S, and the remaining ring atoms being carbon.

The term "leaving group" refers to a functional group or an atom that can be displaced by another functional group in a substitution reaction, such as a nucleophilic substitution reaction. Suitable leaving groups are well known in the art. In a particular embodiment, the leaving group is selected from halogen, $C_1$-$C_6$ alkylsulfonates, $C_1$-$C_6$ haloalkylsulfonates and $(C_1-C_6)$alkyl$(C_6-C_{10})$arylsulfonates, such as chloro, bromo, iodo, mesylate, triflate, tosylate, nosylate and the like.

The term "hydroxyl protecting group" (HPG) refers to a group blocking the OH function for subsequent reactions that can be removed under controlled conditions. Hydroxyl protecting groups are well known in the art. Illustrative examples of hydroxyl protecting groups have been described by Green T W et al. in "Protective Groups in Organic Synthesis", 3rd Edition (1999), Ed. John Wiley & Sons. Virtually any hydroxyl protecting group can be used to put the invention into practice. Illustrative, non-limiting examples of HPGs include:

silyl ethers [—Si(R)(R')(R")]. R, R' and R" can be independently selected from $C_1-C_6$ alkyl, $C_3-C_7$ cycloalkyl, $C_6-C_{10}$ aryl, $C_1-C_6$ alkoxy and halogen. Examples of silyl ethers include trimethylsilyl ether, triethylsilyl ether, tert-butyldimethylsilyl ether, tert-butyldiphenylsilyl ether, tri-isopropylsilyl ether, diethylisopropylsilyl ether, hexyldimethylsilyl ether, triphenylsilyl ether, di-tert-butylmethylsilyl ether;

ethers [—R], including alkoxy and aryloxy methyl ethers [—CH$_2$—OR]. R can be selected from $C_1-C_6$ alkyl, $C_6-C_{10}$ aryl, $(C_6-C_{10})$aryl$(C_1-C_6)$alkyl, $(C_1-C_6)$alkoxy $(C_1-C_6)$alkyl. Examples of ethers include methyl ether, tert-butyl ether, benzyl ether, p-methoxybenzyl ether, 3,4-dimethoxybenzyl ether, trityl ether, allyl ether, methoxymethyl ether, 2-methoxyethoxymethyl ether, benzyloxymethyl ether, p-methoxybenzyloxymethyl ether, methoxyethoxymehtyl ether, 2-(trimethylsilyl) ethoxymethyl ether; tetrahydropyranyl and related ethers;

esters [—COR]. R can be selected from $C_1-C_6$ alkyl, $C_6-C_{10}$ aryl and $(C_6-C_{10})$aryl$(C_1-C_6)$alkyl. Examples of esters include acetate ester, benzoate ester, pivalate ester, methoxyacetate ester, chloroacetate ester, levulinate ester; and carbonates [—COOR]. R can be selected from $C_1-C_6$ alkyl, $C_6-C_{10}$ aryl and $(C_6-C_{10})$aryl$(C_1-C_6)$alkyl. Examples of carbonates include benzyl carbonate, p-nitrobenzyl carbonate, tert-butyl carbonate, 2,2,2-trichloroethyl carbonate, 2-(trimethylsilyl)ethyl carbonate, allyl carbonate.

The term "diol protecting group" refers to a group blocking diol function for subsequent reactions that can be removed under controlled conditions. Diol protecting groups are well known in the art. Illustrative examples of diol protecting groups have been described by Green TW et al. in "Protective Groups in Organic Synthesis", 3rd Edition (1999), Ed. John Wiley & Sons. Virtually any diol protecting group can be used to put the invention into practice. Illustrative, non-limiting examples include:

cyclic acetals and ketals [—C(R)(R')—]. R and R' can be independently selected from hydrogen, $C_1-C_6$ alkyl, $C_6-C_{10}$ aryl and $(C_6-C_{10})$aryl$(C_1-C_6)$alkyl. Examples of cyclic acetals and ketals ethers include methylene acetal, ethylene acetal, tbutylmethylidene acetal, phenyl acetal, p-methoxyphenyl acetal, benzylidene acetal, isopropylidene ketal, tbutylethylidene ketal, phenyl ethylidene ketal, p-methoxyphenyl ethylidene ketal;

ortho esters [—C(R)(R')—]. R can be selected from hydrogen, $C_1-C_6$ alkyl, $C_6-C_{10}$ aryl and $(C_6-C_{10})$aryl $(C_1-C_6)$alkyl, and R' can be selected from $C_1-C_6$ alkoxyl and $C_6-C_{10}$ aryloxy. Examples of ortho esters include methoxymethylene acetal, ethoxymethylene acetal, dimethoxymethylene ortho ester, 1-methoxyethylidene ortho ester, 1-ethoxyethylidene ortho ester, 1,2-dimethoxyethylidene ortho ester, α-methoxybenzylidene ortho ester;

silyl derivatives [—Si(R)(R')—]. R and R' can be independently selected from $C_1-C_6$ alkyl, $C_3-C_7$ cycloalkyl, $C_6-C_{10}$ aryl, $(C_6-C_{10})$aryl$(C_1-C_6)$alkyl, $C_1-C_6$ alkoxy and halogen. Examples of silyl derivatives di-t-butylsilylene, 1-(cyclohexyl)-1-(methyl)silylene, di-isopropylsilylene , dicyclohexylsilylene;

cyclic carbonate [—C(O)—]; and cyclic boronate [—B(R)—]. R can be selected from $C_1-C_6$ alkyl, $C_6-C_{10}$ aryl and $(C_6-C_{10})$aryl$(C_1-C_6)$alkyl. Examples of cyclic boronates include methyl boronate, ethyl boronate, phenyl boronate, and o-acetamidophenyl boranate.

It is noted that while a specific hydroxyl protecting group or diol protecting group is indicated in some steps of the description, other hydroxyl and diol protecting groups are known in the art and are interchangeably useful for the same purpose. Particular hydroxyl and diol protecting groups are mentioned herein as a mere illustration, but further hydroxyl and diol protecting groups known by the skilled person may be used.

As used herein, "orthogonal" when used to describe hydroxyl and/or diol protecting groups of the invention, refers to a strategy well known by the skilled in the art allowing the protection and deprotection of multiple -OH groups one at a time, each with a dedicated set of reaction conditions without affecting the other. Therefore, a first protecting group which is "orthogonal" to a second protecting group means that the first protecting group can be removed from a compound bearing both protecting groups without the second protecting group being removed.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, $C_{1-6}$ alkyl, $C_{3-7}$ cycloalkyl, $C_6-C_{10}$ aryl, 3- to 10-membered heterocyclyl, 3- to 10-membered heteroaryl, halogen, —CN, NO$_2$, CF$_3$, —N(R$_a$)(R$_b$), —OR$_c$, —SR$_d$, —C(O)R$_e$, —C(O)OR$_f$, —C(O)N(R$_g$)(R$_h$), —OC(O)R$_i$; wherein R$_a$, R$_b$, R$_c$, R$_d$, R$_e$, R$_f$, R$_g$, R$_h$ and R$_i$ are independently selected from hydrogen, $C_1-C_6$ alkyl, $C_6-C_{10}$ aryl, 3- to 10-membered heterocyclyl, 3- to 10-membered heteroaryl and trifluoromethyl.

The invention also refers to "salts" of the compounds described in the present description. By way of illustration, said salts can be acid addition salts, base addition salts or metal salts, and can be synthesized from the parent compounds containing a basic or acid moiety by means of conventional chemical processes known in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, trifluoroacetate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts. In a particular embodiment, the salt is an acid addition salt, such as hydrochloride, hydrobromide, hydroiodide, sulfate, nitrate, phosphate, acetate, maleate, fumarate, citrate, oxalate, succinate, tartrate, malate, mandelate, methanesulfonate, p-toluenesulfonate, trifluoroacetate or camphorsulfonate. Preferably, it is selected from HCl, HBr, $H_3PO_4$, $H_2SO_4$, MsOH, pTsOH, TFA, citrate and fumarate salt.

Likewise, the compounds described in the present description can be obtained or used both as free compounds or as solvates (e.g., hydrates, alcoholates, etc.), both forms being included within the scope of the present invention. The solvation methods are generally known in the state of the art. Preferably, the solvate is a hydrate.

The term "organic solvent" includes for example cyclic and acyclic ethers (e.g. $Et_2O$, $iPr_2O$, $tBu_2O$, MeOtBu, 1,4-dioxane, tetrahydrofuran, methyltetrahydrofuran), hydrocarbon solvents (e.g. pentane, hexane, heptane), halogenated solvents (e.g. dichloromethane, chloroform, chlorobenzene), aromatic solvents (e.g. toluene, xylene), ketones (e.g. acetone, butanone, pentanone, methyl ethyl ketone, ethyl isopropyl ketone), esters (e.g. EtOAc, iPrOAc), nitriles (e.g. acetonitrile, benzonitrile), amides (e.g. DMF, DMA, HMPA, NMP), alcohols (e.g. methanol, ethanol, propanol, isopropanol, sec-butanol, t-butanol), sulfoxides (DMSO) and mixtures thereof.

An aspect of the invention is directed to a process for preparing Eldecalcitol, or a salt or solvate thereof, wherein the process comprises:

(A) reaction of a compound of formula (I)

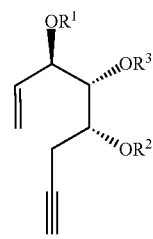

(I)

or a solvate thereof wherein $R^1$, $R^2$ and $R^3$ represent independently a hydroxyl protecting group, wherein $R^3$ is orthogonal to $R^1$ and $R^2$;

with a compound of formula (IX) or with a compound of formula (XXV), or a solvate thereof

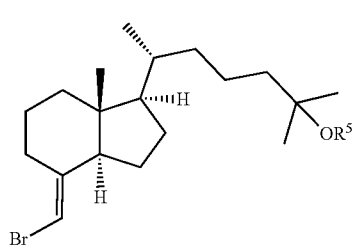

(IX)

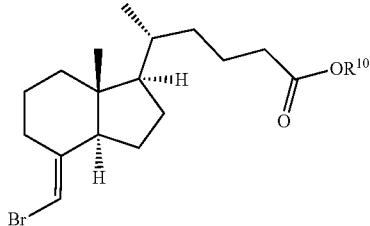

(XXV)

wherein $R^5$ is selected from hydrogen and hydroxyl protecting group, $R^{10}$ is selected from $C_1$-$C_6$ alkyl, $C_6$-$C_{10}$ aryl and ($C_6$-$C_{10}$)aryl($C_1$-$C_6$)alkyl, to provide a compound of formula (X) or a compound of formula (XXVI), respectively, or a solvate thereof

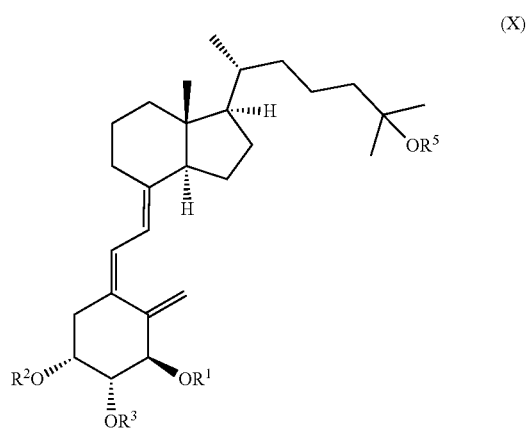

(X)

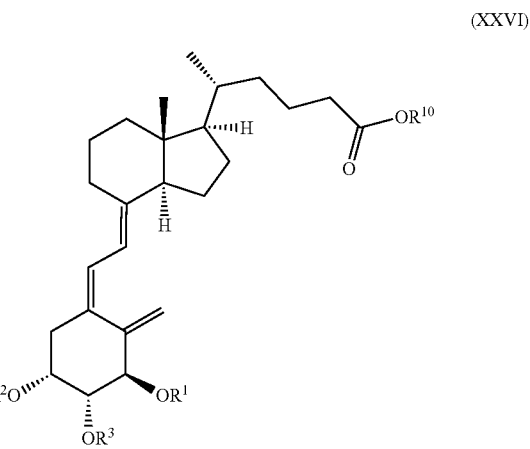

(XXVI)

(B) when a compound of formula (XXVI) or a solvate thereof is obtained, reaction of a compound of formula (XXVI) with MeLi, and optionally protection of the resulting hydroxyl group, to provide a compound of formula (X) or a solvate thereof, (C) cleavage of the hydroxyl protecting group at position 2 in the compound of formula (X), or a solvate thereof, to provide a compound of formula (XI) or a solvate thereof (XI)

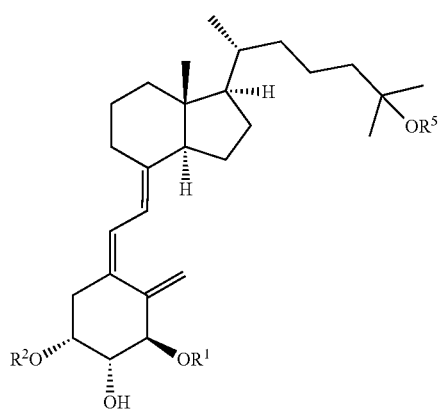

(D) reaction of a compound of formula (XI) with a compound of formula (XII) or with a compound of formula (XXII)

(XII)

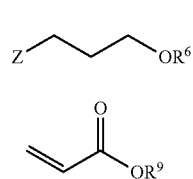

(XXII)

$$\text{(XXII)}$$

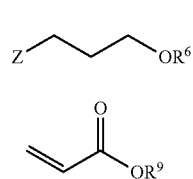

wherein

Z is a leaving group, $R^6$ is selected from hydrogen and hydroxyl protecting group, and $R^9$ is selected from $C_1$-$C_6$ alkyl, $C_6$-$C_{10}$ aryl and ($C_6$-$C_{10}$) aryl($C_1$-$C_6$)alkyl, to provide a compound of formula (XIII), or a compound of formula (XXIII), or a solvate thereof (XIII)

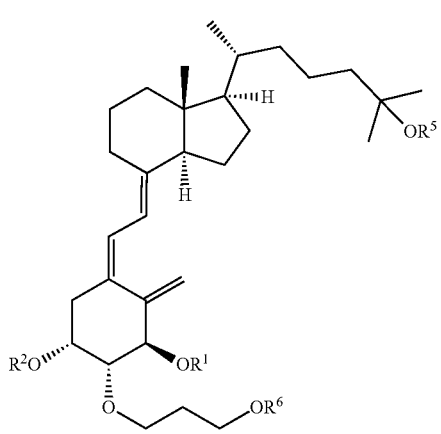

(XXIII)

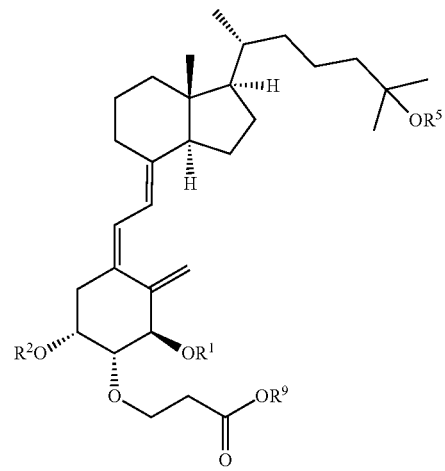

(E) when a compound of formula (XXIII) or a solvate thereof is obtained, reduction of the ester group of a compound of formula (XXIII), or a solvate thereof, to provide a compound of formula (XXIV) or a solvate thereof (XXIV)

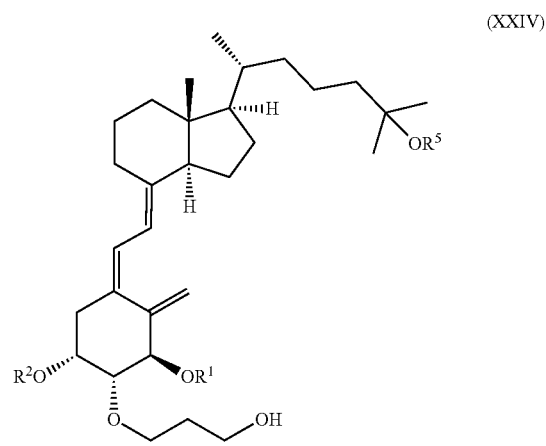

and (F) cleavage of the hydroxyl protecting groups in the compound of formula (XIII), or in the compound of formula (XXIV), or a solvate thereof, to provide Eldecalcitol, or a salt or solvate thereof.

Another aspect of the invention is directed to a process for preparing a compound of formula (I)

(I)

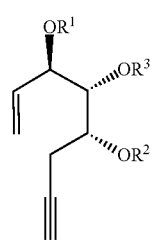

or a solvate thereof wherein $R^1$, $R^2$ and $R^3$ represent independently a hydroxyl protecting group, wherein $R^3$ is orthogonal to $R^1$ and $R^2$, which comprises:

(a) oxidative cleavage of the double bond of a compound of formula (II) or a solvate thereof

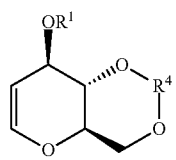
(II)

wherein $R^4$ is a diol protecting group which is orthogonal to $R^1$; to provide a compound of formula (III) or a solvate thereof

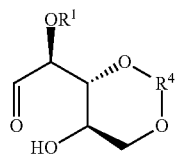
(III)

(b) vinylation of the aldehyde of a compound of formula (III), or a solvate thereof, to provide a compound of formula (IV) or a solvate thereof

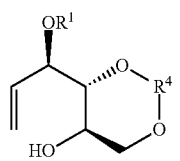
(IV)

(c) protection of the hydroxyl group of a compound of formula (IV), or a solvate thereof, to provide a compound of formula (V) or a solvate thereof

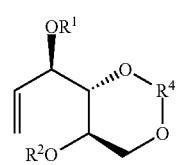
(V)

(d) cleavage of the diol protecting group of a compound of formula (V), or a solvate thereof, to provide a compound of formula (VI) or a solvate thereof

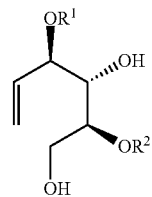
(VI)

(e) conversion of the primary hydroxyl group into the homolog aldehyde and protection of the secondary hydroxyl of a compound of formula (VI), or a solvate thereof, to provide a compound of formula (VII) or a solvate thereof

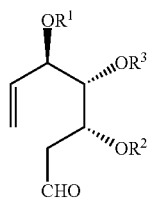
(VII)

and (f) Corey-Fuchs reaction of a compound of formula (VII), or a solvate thereof, to provide a compound of formula (I) or a solvate thereof.

In an embodiment, the process of the invention further comprises converting the resulting compound of formula (I), or a solvate thereof, into Eldecalcitol or a salt or solvate thereof.

In a particular embodiment, further converting the compound of formula (I), or a solvate thereof, into Eldecalcitol or a salt or solvate thereof comprises:

(g) reaction of a compound of formula (I), or a solvate thereof, with a compound of formula (IX) or with a compound of formula (XXV), or a solvate thereof

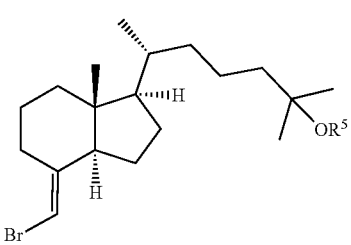
(IX)

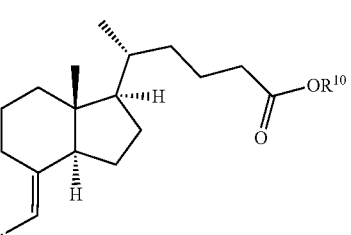
(XXV)

wherein

R[5] is selected from hydrogen and hydroxyl protecting group,

R[10] is selected from $C_1$-$C_6$ alkyl, $C_6$-$C_{10}$ aryl and ($C_6$-$C_{10}$)aryl($C_1$-$C_6$)alkyl, to provide a compound of formula (X) or a compound of formula (XXVI), respectively, or a solvate thereof (X)
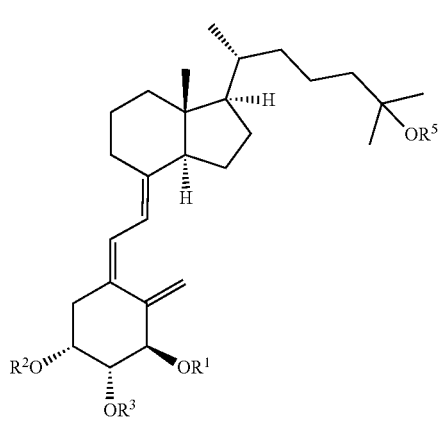

(XXVI)
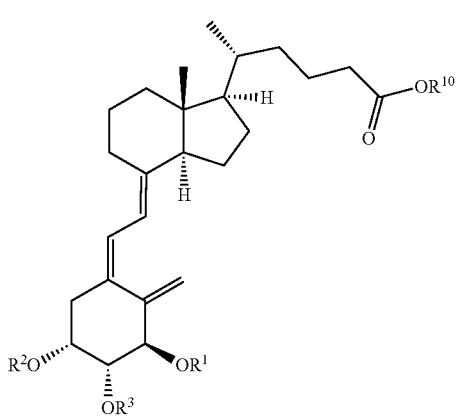

(h) when a compound of formula (XXVI) or a solvate thereof is obtained, reaction of a compound of formula (XXVI) with MeLi, and optionally protection of the resulting hydroxyl group, to provide a compound of formula (X) or a solvate thereof, (i) cleavage of the hydroxyl protecting group at position 2 in the compound of formula (X), or a solvate thereof, to provide a compound of formula (XI) or a solvate thereof (XI)
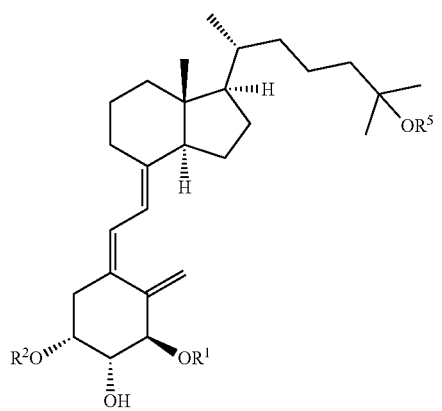

(j) reaction of a compound of formula (XI) with a compound of formula (XII) or with a compound of formula (XXII)

(XII)
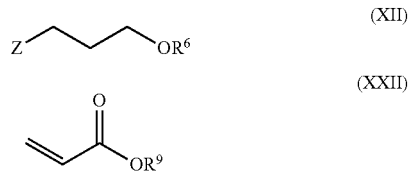

(XXII)

wherein

Z is a leaving group,

R[6] is selected from hydrogen and hydroxyl protecting group, and

R[9] is selected from $C_1$-$C_6$ alkyl, $C_6$-$C_{10}$ aryl and ($C_6$-$C_{10}$)aryl($C_1$-$C_6$)alkyl, to provide a compound of formula (XIII), or a compound of formula (XXIII), or a solvate thereof (XIII)
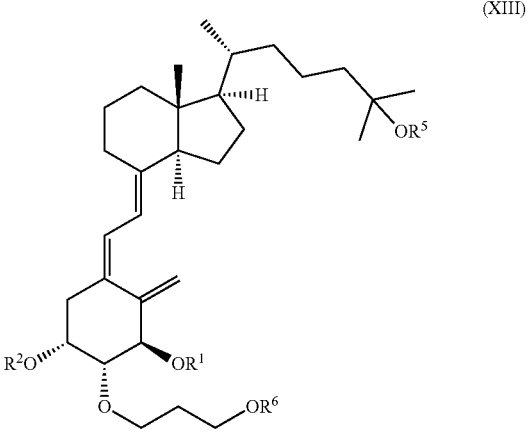

-continued (XXIII)

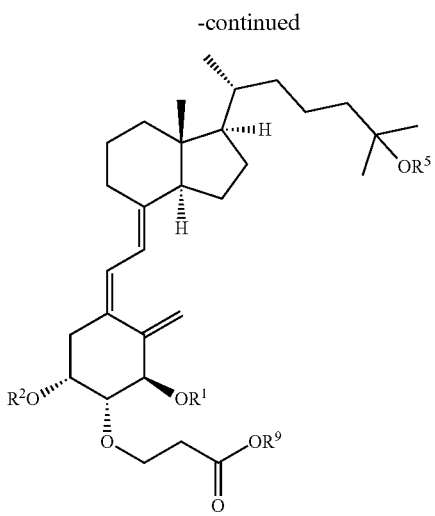

(k) when a compound of formula (XXIII) or a solvate thereof is obtained, reduction of the ester group of a compound of formula (XXIII), or a solvate thereof, to provide a compound of formula (XXIV) or a solvate thereof (XXIV)

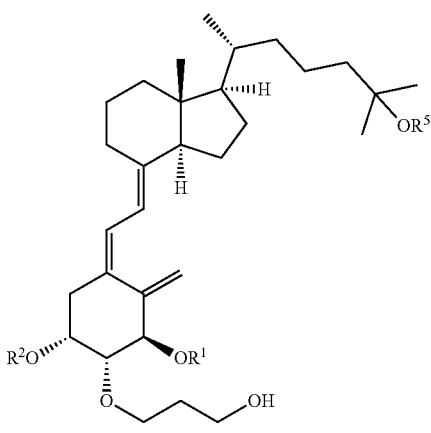

and (l) cleavage of the hydroxyl protecting groups in the compound of formula (XIII), or in the compound of formula (XXV), or a solvate thereof, to provide Eldecalcitol, or a salt or solvate thereof.

In another embodiment, further converting the compound of formula (I), or a solvate thereof, into Eldecalcitol or a salt or solvate thereof comprises converting the compound of formula (I), or a solvate thereof, into a compound of formula (XV) or a solvate thereof, which can be converted into Eldecalcitol or a salt or solvate thereof by methods disclosed in the prior art. In a preferred embodiment, said process comprises:

(g') cleavage of the silyl protecting group in a compound of formula (I), or a solvate thereof, to provide a compound of formula (XIV)

(XIV)

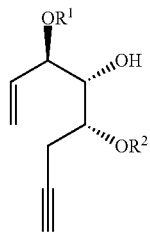

or a solvate thereof wherein $R^1$ and $R^2$ represent independently a hydroxyl protecting group;

(h') reaction of a compound of formula (XIV), or a solvate thereof, with a compound of formula (XII)

(XII)

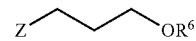

wherein

Z is a leaving group, and $R^6$ is selected from hydrogen and hydroxyl protecting group, to provide a compound of formula (XV) or a solvate thereof (XV)

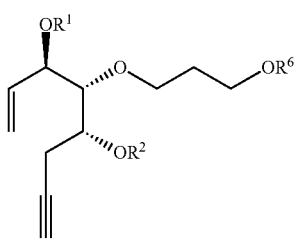

(i') reaction of a compound of formula (XV), or a solvate thereof, with a compound of formula (IX) or with a compound of formula (XXV), or a solvate thereof (IX)

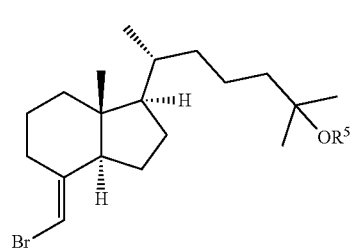

-continued

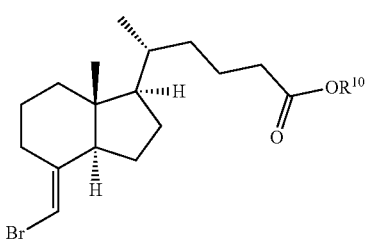

(XXV)

wherein

R⁵ is selected from hydrogen and hydroxyl protecting group, $R^{16}$ is selected from $C_1$-$C_6$ alkyl, $C_6$-$C_{10}$ aryl and ($C_6$-$C_{10}$)aryl($C_1$-$C_6$)alkyl, to provide a compound of formula (XIII) or a compound of formula (XXVII), respectively, or a solvate thereof

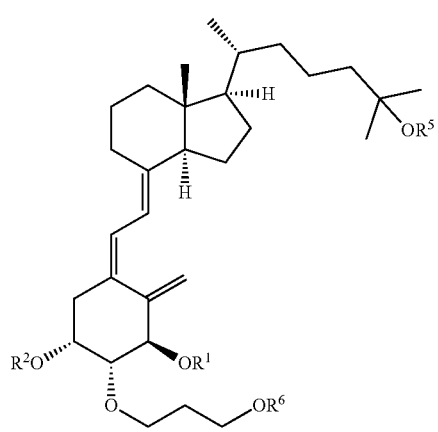

(XIII)

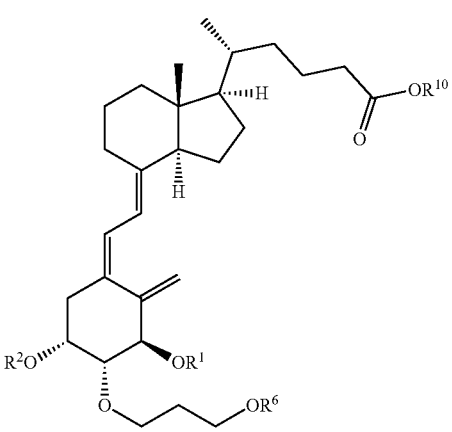

(XXVII)

(j') when a compound of formula (XXVII) or a solvate thereof is obtained, reaction of a compound of formula (XXVII) with MeLi, and optionally protection of the resulting hydroxyl group, to provide a compound of formula (XIII) or a solvate thereof, (k') cleavage of the hydroxyl protecting groups in the compound of formula (XIII), or a solvate thereof, to provide Eldecalcitol, or a salt or solvate thereof.

In an embodiment of the invention, $R^1$, $R^2$ and $R^3$ represent independently a hydroxyl protecting group selected from
—Si(R)(R')(R"), wherein R, R' and R" are independently selected from $C_1$-$C_6$ alkyl, $C_3$-$C_7$ cycloalkyl, $C_6$-$C_{10}$ aryl, $C_1$-$C_6$ alkoxy and halogen,
$C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
—$CH_2$—$OR^a$, wherein $R^a$ is selected $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
—$COR^b$, wherein $R^b$ is selected from $C_1$-$C_6$ alkyl, $C_6$-$C_{10}$ aryl and ($C_6$-$C_{10}$)aryl($C_1$-$C_6$)alkyl, and
—$COOR^c$, wherein $R^c$ is selected from $C_1$-$C_6$ alkyl, $C_6$-$C_{10}$ aryl and ($C_6$-$C_{10}$)aryl($C_1$-$C_6$)alkyl;
with the proviso that $R^3$ is orthogonal to $R^1$ and $R^2$.

In a particular embodiment, $R^1$ and $R^2$ represent independently a hydroxyl protecting group selected from:
$C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
—$CH_2$-$OR^a$, wherein $R^a$ is selected $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
—$COR^b$, wherein $R^b$ is selected from $C_1$-$C_6$ alkyl, $C_6$-$C_{10}$ aryl and ($C_6$-$C_{10}$)aryl($C_1$-$C_6$)alkyl, and
—$COOR^c$, wherein $R^c$ is selected from $C_1$-$C_6$ alkyl, $C_6$-$C_{10}$ aryl and ($C_6$-$C_{10}$)aryl($C_1$-$C_6$)alkyl; and
$R^3$ is a hydroxyl protecting group as defined herein that is orthogonal to $R^1$ and $R^2$. Preferably, $R^3$ represents —Si(R)(R')(R"), wherein R, R' and R" are independently selected from $C_1$-$C_6$ alkyl, $C_3$-$C_7$ cycloalkyl, $C_6$-$C_{10}$ aryl, $C_1$-$C_6$ alkoxy and halogen.

In another embodiment, $R^1$ and $R^2$ are independently selected from $C_1$-$C_6$ alkyl, $C_6$-$C_{10}$aryl, ($C_6$-$C_{10}$)aryl($C_1$-$C_6$)alkyl, ($C_1$-$C_6$)alkoxy($C_1$-$C_6$)alkyl and ($C_6$-$C_{10}$aryloxy($C_1$-$C_6$)alkyl; more preferably from ($C_1$-$C_6$)alkoxy($C_1$-$C_6$)alkyl; even more preferably are MOM.

In a further embodiment, $R^3$ represents —Si(R)(R')(R"), wherein R, R' and R" are independently selected from $C_1$-$C_6$ alkyl; more preferably from $C_1$-$C_3$ alkyl.

In a particular embodiment of the invention, $R^4$ is selected from a diol protecting group of formula:
—C(R)(R')—, wherein R and R' are independently selected from hydrogen, $C_1$-$C_6$ alkyl, $C_6$-$C_{10}$ aryl and ($C_6$-$C_{10}$)aryl($C_1$-$C_6$)alkyl,
—C(R)(R')—, wherein R is selected from hydrogen, $C_1$-$C_6$ alkyl, $C_6$-$C_{10}$ aryl and ($C_6$-$C_{10}$)aryl($C_1$-$C_6$)alkyl, and R' is selected from $C_1$-$C_6$ alkoxyl and $C_6$-$C_{10}$ aryloxy,
—Si(R)(R')—, wherein R and R' are independently selected from $C_1$-$C_6$ alkyl, $C_3$-$C_7$ cycloalkyl, $C_6$-$C_{10}$aryl, ($C_6$-$C_{10}$)aryl($C_1$-$C_6$)alkyl, $C_1$-$C_6$ alkoxy and halogen,
—C(O)—, and
—B(R)—, wherein R is selected from $C_1$-$C_6$ alkyl, $C_6$-$C_{10}$ aryl and ($C_6$-$C_{10}$)aryl($C_1$-$C_6$)alkyl,
with the proviso that it is orthogonal to $R^1$.

In a particular embodiment, $R^4$ is a group of formula —Si(R)(R')—, wherein R and R' are independently selected from $C_1$-$C_6$ alkyl, $C_3$-$C_7$ cycloalkyl, $C_6$-$C_{10}$ aryl, ($C_6$-$C_{10}$)aryl($C_1$-$C_6$)alkyl, $C_1$-$C_6$ alkoxy and halogen; preferably are independently selected from $C_1$-$C_6$ alkyl.

According to a particular embodiment of the invention, $R^1$ and $R^2$ represent independently a hydroxyl protecting group selected from:
$C_1$-$C_6$ alkyl, $C_6$-$C_{10}$aryl, ($C_6$-$C_{10}$)aryl($C_1$-$C_6$)alkyl and ($C_1$-$C_6$)alkoxy($C_1$-$C_6$)alkyl, —CH$_2$-OR$^a$, wherein R$^a$ is selected C$_1$-C$_6$ alkyl, C$_6$-C$_{10}$ aryl, (C$_6$-C$_{10}$)aryl(C$_1$-C$_6$)alkyl and (C$_1$-C$_6$)alkoxy(C$_1$-C$_6$)alkyl, —COR$^b$, wherein R$^b$ is selected from C$_1$-C$_6$ alkyl, C$_6$-C$_{10}$ aryl and (C$_6$-C$_{10}$)aryl(C$_1$-C$_6$)alkyl, and —COOR$^c$, wherein R$^c$ is selected from C$_1$-C$_6$ alkyl, C$_6$-C$_{10}$ aryl and (C$_6$-C$_{10}$)aryl(C$_1$-C$_6$)alkyl;

R$^3$ represents —Si(R)(R')(R"), wherein R, R' and R" are independently selected from C$_1$-C$_6$ alkyl, C$_3$-C$_7$ cycloalkyl, C$_6$-C$_{10}$ aryl, C$_1$-C$_6$ alkoxy and halogen; and R$^4$ is a group of formula —Si(R)(R')—, wherein R and R' are independently selected from C$_1$-C$_6$ alkyl, C$_3$-C$_7$ cycloalkyl, C$_6$-C$_{10}$ aryl, (C$_6$-C$_{10}$)aryl(C$_1$-C$_6$)alkyl, C$_1$-C$_6$ alkoxy and halogen.

In an embodiment of the invention, R$^5$ and R$^6$ represent independently hydrogen or a hydroxyl protecting group selected from:

—Si(R)(R')(R"), wherein R, R' and R" are independently selected from C$_1$-C$_6$ alkyl, C$_3$-C$_7$ cycloalkyl, C$_6$-C$_{10}$ aryl, C$_1$-C$_6$ alkoxy and halogen, C$_1$-C$_6$ alkyl, C$_6$-C$_{10}$ aryl, (C$_6$-C$_{10}$)aryl(C$_1$-C$_6$)alkyl and (C$_1$-C$_6$)alkoxy(C$_1$-C$_6$)alkyl, —CH$_2$-OR$^a$, wherein R$^a$ is selected C$_1$-C$_6$ alkyl, C$_6$-C$_{10}$ aryl, (C$_6$-C$_{10}$)aryl(C$_1$-C$_6$)alkyl and (C$_1$-C$_6$)alkoxy(C$_1$-C$_6$)alkyl, —COR$^b$, wherein R$^b$ is selected from C$_1$-C$_6$ alkyl, C$_6$-C$_{10}$ aryl and (C$_6$-C$_{10}$)aryl(C$_1$-C$_6$)alkyl, and —COOR$^c$, wherein R$^c$ is selected from C$_1$-C$_6$ alkyl, C$_6$-C$_{10}$ aryl and (C$_6$-C$_{10}$)aryl(C$_1$-C$_6$)alkyl.

In a particular embodiment of the invention, when R$^5$ is a hydroxyl protecting group, R$^3$ is orthogonal to R$^5$.

In a particular embodiment, R$^9$ is selected from C$_1$-C$_6$ alkyl and (C$_6$-C$_{10}$)aryl(C$_1$-C$_6$)alkyl; preferably from C$_1$-C$_3$ alkyl and (C$_6$-C$_{10}$)aryl(C$_1$-C$_3$)alkyl. In an embodiment, R$^9$ is C$_1$-C$_3$ alkyl, such as methyl or ethyl.

In a particular embodiment, R$^{10}$ is selected from C$_1$-C$_6$ alkyl and (C$_6$-C$_{10}$)aryl(C$_1$-C$_6$)alkyl; preferably from C$_1$-C$_3$ alkyl and (C$_6$-C$_{10}$)aryl(C$_1$-C$_3$)alkyl. In an embodiment, R$^{10}$ is C$_1$-C$_3$ alkyl, such as methyl or ethyl.

In a particular embodiment of the invention, R$^1$, R$^2$, R$^5$ and R$^6$ are MOM, and R$^3$ is TES. Preferably, R$^9$ and R$^{10}$ are methyl or ethyl.

In a preferred embodiment, Z is a leaving group selected from halogen, C$_1$-C$_6$ alkylsulfonates, C$_1$-C$_6$ haloalkylsulfonates and (C$_1$-C$_6$)alkyl(C$_6$-C$_{10}$)arylsulfonates; more preferably chloro, bromo, iodo, mesylate, triflate, tosylate and nosylate.

In a particular embodiment, step (a) is carried out by treating a compound of formula (II), or a solvate thereof, with ozone followed by cleavage of the resulting ozonide. Preferably, said cleavage is carried out by treatment with a reductive reagent such as tri(C$_1$-C$_6$ alkyl)phosphines, tri(C$_6$-C$_{10}$ aryl)phosphines, di(C$_1$-C$_6$ alkyl)sulfides, thiourea or Zn/acetic acid; more preferably by treatment with triphenyl phosphine, trimethylphosphine, tributylphosphine, dimethyl sulfide, thiourea or Zn/acetic acid.

In an embodiment, the molar ratio of the reductive reagent with respect to the compound of formula (II) is from 1:1 to 6:1.

Preferably, step (a) is performed in the presence of an organic solvent and at a temperature between −78° C. and 40° C.

According to an embodiment, the crude reaction mixture from step (a) is used as a starting material for the subsequent step without purification.

Vinylation reactions of aldehydes and suitable reaction conditions are known in the art (e.g. M. B. Smith, J. March, March's Advanced Organic Chemistry, Wiley-Interscience, 5$^{th}$ ed., pp. 1541-1542; Science of Synthesis: Houben-Weyl methods of molecular transformations, Thieme). In an embodiment, step (b) is carried out by reacting a compound of formula (III), or a solvate thereof, with a compound of formula (XVIII), (XIX) or (XX)

(XVIII)

(XIX)

(XX)

wherein

X is halogen, preferably Br;

each R' is selected from C$_6$-C$_{10}$ aryl, preferably phenyl; and each R" is selected from C$_1$-C$_6$ alkyl and (C$_6$-C$_{10}$)aryl(C$_1$-C$_6$)alkyl, preferably methyl or ethyl, in the presence of a base.

Suitable bases include organolithium bases, alkali metal hydrides and alkali metal alcoholates, such as e.g. nBuLi, tBuLi, sBuLi, MeLi, PhLi, LDA, NaH, NaOtBu, KOtBu, NaOMe, NaOEt.

Preferably, the reaction is carried out in the presence of an organic solvent, such as for example a cyclic or acyclic ether (e.g. Et$_2$O, iPr$_2$O, tBu$_2$O, 1,4-dioxane, tetrahydrofuran, methyltetrahydrofuran), a hydrocarbonated solvent (e.g. pentane, hexane), a halogenated solvent (e.g. dichloromethane, chloroform), an aromatic solvent (e.g. toluene, xylene), dimethylformamide, dimethylacetamide or mixtures thereof. In a particular embodiment, the reaction is performed in the presence of an ether, such as THF. In an embodiment, the reaction is carried out at a temperature between −40° C. and 80° C., preferably between −20° C. and 40° C.

In an embodiment, the molar ratio of the compound of formula (XVIII), (XIX) or (XX) with respect to the compound of formula (III) is from 1:1 to 8:1, preferably from 2:1 to 5:1.

In an embodiment, step (e) comprises conversion of the primary hydroxyl group into the homolog nitrile, and optionally protection of the secondary hydroxyl group, to provide a compound of formula (XVI) or a solvate thereof

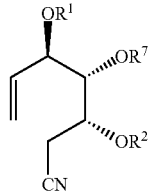

(XVI)

wherein R$^7$ is selected from hydrogen and R$^3$ as defined above, or a solvate thereof, and reduction of the nitrile group of a compound of formula (XVI), or a solvate thereof, and optionally protection of the secondary hydroxyl group to provide aldehyde (VII), or a solvate thereof. That is, protection of the hydroxyl group to provide the group OR³ can be performed either before or after reduction of the nitrile group.

In a particular embodiment, step (e) comprises conversion of the primary hydroxyl group of a compound of formula (VI), or a solvate thereof, into a leaving group to provide a compound of formula (XVII) or a solvate thereof

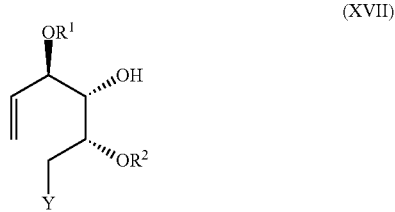

(XVII)

wherein Y is a leaving group;
conversion of the leaving group into nitrile, reduction of the of the nitrile group, and optionally protection of the secondary hydroxyl group either before conversion of the leaving group into nitrile or before reduction of the nitrile or after reduction of the nitrile group to provide aldehyde (VII), or a solvate thereof.

In an embodiment, protection of the secondary hydroxyl group as OR³ is performed after conversion of the leaving group into nitrile and before reduction of said nitrile to aldehyde.

Conversion of the primary hydroxyl group of a compound of formula (VI), or a solvate thereof, into a leaving group can be carried out by conventional means known in the art. For example, a compound of formula (XVII) wherein the leaving group is halogen can be obtained by treatment with I₂, NaI, Br₂, CBr₄, PBr₃, Cl₂, SOCl₂. A compound of formula (XVII) wherein the leaving group is a sulfonate can be obtained by treatment with a sulphonyl chloride, such as TsCl or MsCl. Conversion into a leaving group is preferably carried out in the presence of an organic solvent at a temperature from −78° C. to 80° C., preferably from −40° C. to 40° C.

In an embodiment, a compound of formula (XVII), or a solvate thereof, wherein Y is I is obtained by treatment with I₂ and PPh₃, preferably in the presence of imidazole and an organic solvent.

Conversion of the leaving group into a nitrile can be carried out by known means. For example, by treatment with NaCN or KCN in an organic solvent, such as a cyclic or acyclic ether (e.g. Et₂O, iPr₂O, tBu₂O, MeOtBu, 1,4-dioxane, tetrahydrofuran, methyltetrahydrofuran), halogenated solvent (e.g. dichloromethane, chloroform, chlorobenzene), ketone (e.g. acetone, butanone, pentanone, methyl ethyl ketone, ethyl isopropyl ketone), ester (e.g. EtOAc, iPrOAc), nitrile (e.g. acetonitrile, benzonitrile), amide (e.g. DMF, DMA, HMPA, NMP), alcohol (e.g. methanol, ethanol, propanol, isopropanol, sec-butanol, t-butanol), sulfoxide (DMSO) and mixtures thereof.

In an embodiment the reaction is carried out a temperature from 0° C. to 150° C., preferably from 10° C. to 80° C. In an embodiment, the molar ratio of NaCN or KCN with respect to the compound having the leaving group is from 1:1 to 6:1.

Reduction of the nitrile group to aldehyde can be carried out by known means. In an embodiment, it is carried out in the presence of a metal hydride, such as DIBAL, LiAlH₄, LiAlH(OEt)₃, LiAlH(OMe)₃, LiAlH(OtBu)₃ or NaBH₄, preferably DIBAL. The reduction is preferably performed in the presence of an organic solvent and at a temperature from −78° C. to 50° C., preferably from −78° C. to 0° C.

In an embodiment, the molar ratio of metal hydride with respect to the nitrile is from 1:1 to 3:1, preferably from 1:1 to 1.5:1.

According to an embodiment, step (f) comprises first treating a compound of formula (VII), or a salt or solvate thereof, with CBr₄ in the presence of PPh₃ to provide the corresponding dibromo-olefin. Said reaction is preferably carried out in the presence of an organic solvent, such as preferably a cyclic or acyclic ethers (e.g. Et₂O, iPr₂O, tBu₂O, MeOtBu, 1,4-dioxane, tetrahydrofuran, methyltetrahydrofuran), a hydrocarbon solvent (e.g. pentane, hexane, heptane), a halogenated solvent (e.g. dichloromethane, chloroform, chlorobenzene), and preferably at a temperature between −78° C. and 50° C., more preferably between −20° C. and 40° C.

The resulting dibromo-olefin can be converted into a compound of formula (I), or a solvate thereof, by treatment with a base. Preferably, the base is selected from nBuLi, tBuLi, sBuLi, MeLi, PhLi, HMDSLi and LDA. The reaction can be carried out in the presence of an organic solvent, preferably a cyclic or acyclic ethers (e.g. Et₂O, iPr₂O, tBu₂O, MeOtBu, 1,4-dioxane, tetrahydrofuran, methyltetrahydrofuran), a hydrocarbon solvent (e.g. pentane, hexane, heptane), a halogenated solvent (e.g. dichloromethane, chloroform, chlorobenzene), and preferably at a temperature between −78° C. and 50° C., more preferably between −78° C. and 20° C.

Reaction of a compound of formula (I) or (XV), or a solvate thereof, with a compound of formula (IX), or with a compound of formula (XXV), or a solvate thereof (steps (A), (g) and (i')), may be carried out in the presence of a Pd catalyst by means known in the prior art. In an embodiment, the reaction is carried out in the presence of a Pd(0) catalyst, such as Pd(PPh₃)₄, Pd₂(dba)₃ or Pd₂(dba)₃·CHCl₃, preferably in the presence of a base, including an organic (e.g. tertiary amines, such as Me₃N, Et₃N, Bu₃N, iPr₂NEt, Cy₂NMe, pyridine) or an inorganic base (e.g. Cs₂CO₃, K₂CO₃, Na₂CO₃, Ag₂CO₃, K₃PO₄, NaOH, KOH, CsOH). In an embodiment, the reaction is carried out also in the presence of a trialkyl or friaryl phosphine, preferably PPh₃. Preferably, the reaction is carried out in the presence of an organic solvent.

In a particular embodiment, this reaction is carried out in the presence of Pd(PPh₃)₄, Et₃N and preferably an organic solvent (e.g. toluene), or in the presence of Pd₂(dba)₃·CHCl₃, Et₃N, PPh₃ and preferably an organic solvent (e.g. toluene), or in the presence of Pd₂(dba)₃, Et₃N and preferably an organic solvent (e.g. toluene). In a preferred embodiment, this reaction is carried out in the presence of Pd(PPh₃)₄, Et₃N and preferably an organic solvent (e.g. toluene).

This reaction may be carried out, for example, at a temperature from 20° C. to 150° C., preferably from 80° C. to 130° C.

In an embodiment, reaction of a compound of formula (XI) or (XIV), or a solvate thereof, with a compound of formula (XII) or a solvate thereof (steps (D), (j) and (h')), may be carried out in the presence of a base and an organic solvent.

Suitable bases include inorganic and organic bases, such as an alkali metal carbonate or bicarbonate (e.g. Na₂CO₃, K₂CO₃, Cs₂CO₃, Li₂CO₃, NaHCO₃, KHCO₃, CsHCO₃, LiHCO₃), an alkali metal phosphate (e.g. Na₃PO₄, K₃PO₄, Na₂HPO₄, K₂HPO₄, NaH₂PO₄, KH₂PO₄), an alkali metal alkoxide (e.g. NaOMe, KOMe, NaOEt, KOEt, NaOtBu, KOtBu), an alkali metal hydroxide (e.g. NaOH, KOH, LiOH, CsOH), an aliphatic or aromatic amine (e.g. Me$_2$NH, Et$_2$NH, iPr$_2$NH, Bu$_2$NH, Me$_3$N, Et$_3$N, Bu$_3$N, iPr$_2$EtN, N-methylmorpholine, pyridine, DMAP, aniline, N,N-dimethylaniline). Preferably, the base is an inorganic base.

In an embodiment, the organic solvent is a polar organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), alcohol (e.g. methanol, ethanol, propanol, isopropanol, sec-butanol, t-butanol), or mixtures thereof. In a further embodiment, the organic solvent is a polar aprotic organic solvent, such as THF, a ketone (e.g. acetone, butanone, pentanone, methyl ethyl ketone, ethyl isopropyl ketone), an ester (e.g. EtOAc, iPrOAc), a nitrile (e.g. acetonitrile, benzonitrile), an amide (e.g. DMF, DMA, HMPA, NMP), a sulfoxide (DMSO), or mixtures thereof.

In a preferred embodiment, the reaction is carried out in the presence of an inorganic base and a polar organic solvent, more preferably a polar aprotic organic solvent.

In an embodiment, the reaction is performed at a temperature between 0° C. and 150° C., preferably at a temperature between 0° C. and 100° C., more preferably between 10° C. and 50° C.

In an embodiment, reaction of a compound of formula (XI), or a solvate thereof, with a compound of formula (XXII) or a solvate thereof (steps (D) and (j)), may be carried out in the presence of a base and an organic solvent.

Suitable bases include inorganic and organic bases, such as an alkali metal carbonate or bicarbonate (e.g. Na$_2$CO$_3$, K$_2$CO$_3$, Cs$_2$CO$_3$, Li$_2$CO$_3$, NaHCO$_3$, KHCO$_3$, CsHCO$_3$, LiHCO$_3$), an alkali metal phosphate (e.g. Na$_3$PO$_4$, K$_3$PO$_4$, Na$_2$HPO$_4$, K$_2$HPO$_4$, NaH$_2$PO$_4$, KH$_2$PO$_4$), an alkali metal alkoxide (e.g. NaOMe, KOMe, NaOEt, KOEt, NaOtBu, KOtBu), an alkali metal hydroxide (e.g. NaOH, KOH, LiOH, CsOH), an aliphatic or aromatic amine (e.g. Me$_2$NH, Et$_2$NH, iPr$_2$NH, Bu$_2$NH, Me$_3$N, Et$_3$N, Bu$_3$N, iPr$_2$EtN, N-methylmorpholine, pyridine, DMAP, aniline, N,N-dimethylaniline). Preferably, the base is an inorganic base, more preferably an alkali metal hydroxide, such as NaOH.

In an embodiment, the organic solvent is selected from cyclic and acyclic ethers (e.g. Et$_2$O, iPr$_2$O, tBu$_2$O, MeOtBu, 1,4-dioxane, tetrahydrofuran, methyltetrahydrofuran), hydrocarbon solvents (e.g. pentane, hexane, heptane), halogenated solvents (e.g. dichloromethane, chloroform, chlorobenzene), aromatic solvents (e.g. toluene, xylene) and mixtures thereof. Preferably, toluene.

In an embodiment, the reaction is performed at a temperature between 0° C. and 100° C., preferably at a temperature between 0° C. and 60° C., preferably between 10° C. and 50° C.

Reduction of the ester group in the compound of formula (XXIII), or a solvate thereof, to the alcohol (XXIV), or a solvate thereof, can be carried out by known means. In an embodiment, it is carried out in the presence of a metal hydride, such as DIBAL, LiAlH$_4$, LiAlH(OEt)$_3$, LiAlH(OMe)$_3$, or LiAlH(OtBu)$_3$, preferably DIBAL or LiAlH$_4$; more preferably DIBAL. The reduction is preferably performed in the presence of an organic solvent and at a temperature from −100° C. to 50° C., preferably from −78° C. to 0° C., more preferably between −78° C. and −20° C.

In an embodiment, the molar ratio of metal hydride with respect to the nitrile is from 2:1 to 6:1, preferably from 2:1 to 4:1.

Conversion of a compound of formula (XXVI), or a solvate thereof, into a compound of formula (X), or a solvate thereof, and conversion of a compound of formula (XXVII), or a solvate thereof, into a compound of formula (XIII), or a solvate thereof, can be carried out by reaction with MeLi in an organic solvent.

In an embodiment, the organic solvent is selected from cyclic and acyclic ethers (e.g. Et$_2$O, iPr$_2$O, tBu$_2$O, MeOtBu, 1,4-dioxane, tetrahydrofuran, methyltetrahydrofuran), hydrocarbon solvents (e.g. pentane, hexane, heptane), halogenated solvents (e.g. dichloromethane, chloroform, chlorobenzene), aromatic solvents (e.g. toluene, xylene) and mixtures thereof. Preferably, a cyclic or acyclic ether such as THF.

In an embodiment, the reaction is performed at a temperature between −100° C. and 30° C., preferably between −78° C. and 0° C., more preferably between −78° C. and −20° C.

In an embodiment, the molar ratio of MeLi with respect to the compound of formula (XXVI) or (XXVII) is from 2:1 to 5:1, preferably from 2:1 to 3:1.

After reaction of the compound of formula (XXVI) or (XXVII), or a solvate thereof, with MeLi, a compound of formula (X) or (XIII), respectively, or a solvate thereof, wherein R$^5$ is hydrogen is obtained. Said hydroxyl group can be optionally protected by known means to provide a compound of formula (X) or (XIII), respectively, or a solvate thereof, wherein R$^5$ is a hydroxyl protecting group.

Compounds of formula (II) in the present invention can be obtained by known means. For instance, by protection of the hydroxyl group of a compound of formula (XXI) or a solvate thereof

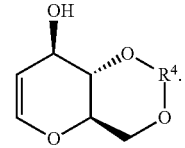

(XXI)

Compounds of formula (XXI) are known in the art (e.g. WO 2008/025160, Journal of Organic Chemistry 2018, 83, 5187-5198). In a particular embodiment, they can be obtained from commercially available tri-O-acetyl-D-glucan by cleave of the acetyl groups followed by protection of the 1,3-diol.

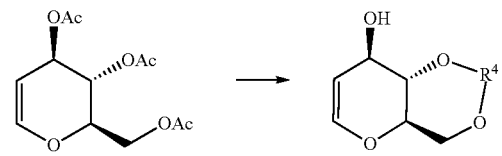

Compounds of formula (IX) and (XXV) used for the subsequent preparation of Eldecalcitol are known in the art (e.g. Heterocycles 2009, 79, 145-162; Heterocycles 2006, 70, 295-307; Anticancer Research 2009, 29, 3571-3578).

If needed during the process of the invention, protection and/or deprotection of the hydroxyl groups and the diol group can be performed at any stage of the synthesis. The most suitable stage for said protection and/or deprotection can be readily determined by those skilled in the art.

Protection/cleavage of the hydroxyl and diol protecting groups can be carried out by any conventional means known in the art (e.g. T. H. Greene and P. G. M. Wuts, Protective Groups in Organic Synthesis, 4$^{th}$ edition, John Wiley & Sons, 2007).

For example, when the hydroxyl or the diol protecting group is an ester (COR) or a carbonate (COOR, —C(O)—), it can be easily deprotected by hydrolysis in basic or acid media according to well-established procedures of the state of the art.

When the hydroxyl or the diol protecting group is a silyl ether (Si(R)(R')(R"), —Si(R)(R')—), it can be easily deprotected by the use of fluoride reagents such as fluoride salts (e.g. TBAF) or HF, acid media, oxidizing media, etc.

When the hydroxyl or the diol protecting group is an ether (R), an acetal, a ketal or an orhto ester (—C(R)(R')—), it can be easily deprotected through hydrolysis in acid media (for example, for methyl ethers ($CH_2OR$)), hydrogenation (for example, for benzyl ethers or benzylidene acetal), oxidation (for example, for aryl ethers), etc.

It should be understood that the scope of the present disclosure includes all the possible combinations of embodiments disclosed herein.

EXAMPLES

Synthesis of (4aR,8R,8aS)-2,2-di-tert-butyl-4,4a,8,8a-tetrahydropyrano[3,2-d][1,3,2]dioxasilin-8-ol (1)

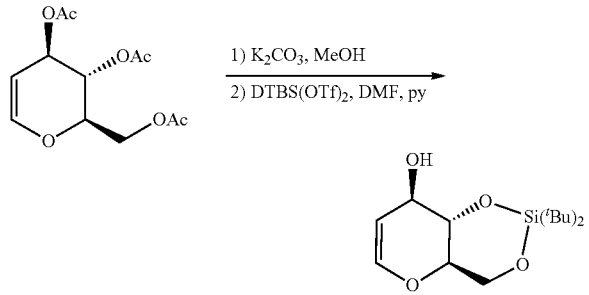

To a solution of (+)-Tri-O-acetyl-D-glucal (14g, 51.4 mmol) in MeOH (50 mL) was added $K_2CO_3$ (100 mg) and the mixture was stirred for 12 h at room temperature. Then, MeOH was evaporated under reduced pressure and the resultant residue was dissolved in $CHCl_3$ and concentrated again for three times. The resulting solid was dissolved in DMF (40 ml), pyridine (20 mL, 257.1 mmol) was added and cooled to −40° C. Then, terc-$Bu_2Si(OTf)_2$ (18.3 mL, 56.6 mmol) was dropwise added and the mixture was stirred for 1 h till room temperature. After that time, EtOAc (30 mL) was added and the organic layer washed with a 15% aqueous solution of $CuSO_4$ (2×30 mL), water (3×30 mL) and dried over $Na_2SO_4$, filtered and the solvent evaporated under reduced pressure. The residue was purified by column chromatography with ethyl acetate-hexane (5%) to give compound 1 (13.4 g, 91%) as a white solid (Mp: 84-85° C.), Rf: 0.71 (EtOAc). IR (ATR, cm$^{-1}$): 3440, 2988, 2285, 1646, 1215, 869. $^1$H-NMR ($CDCl_3$, δ): 6.25 (1H, dd, J=6.1/1.8 Hz, H-1), 4.74 (1H, dd, J=6.1/1.9 Hz, H-2), 4.25 (1H, m, H-3), 4.16 (1H, dd, J=10.2/4.9 Hz, H-6), 3.93 (2H, m, H-6, H-4), 3.82 (1H, m, H-5), 2.66 (1H, s, OH); 1.05 (9H, s, $CH_3$-$^t$Bu), 0.98 (9H, s, $CH_3$-$^t$Bu) ppm. $^{13}$C-NMR ($CDCl_3$, δ): 143.5 (CH-1), 103.1 (CH-2), 77.3 (CH-4), 72.2 (CH-5), 70.0 (CH-3), 65.6 ($CH_2$-6), 27.4 ($CH_3$-$^t$Bu), 26.8 ($CH_3$-$^t$Bu), 22.6 (C-$^t$Bu), 19.7 (C-$^t$Bu) ppm. MS(ESI) [m/z, (%)]: 287 (M$^+$+1, 7), 286 (M$^+$, 12), 269 (M$^+$—OH, 100). HRMS (ESI): 286.1232 calculated for $C_{14}H_{26}O_4Si$, found 286.1647.

Synthesis of (4aR,8R,8aS)-2,2-di-tert-butyl-8-(methoxymethoxy)-4,4a,8,8a-tetrahydropyrano[3,2-d][1,3,2]dioxasiline (2)

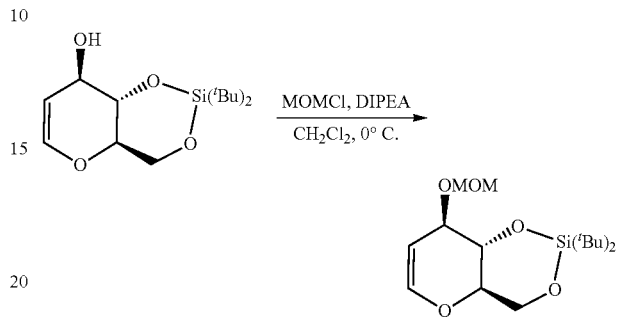

To a solution of 1 (1.03 g, 3.6 mmol) in $CH_2CH_2$ (7 ml) cooled to 0° C. was added dropwise DIPEA (1.9 ml, 10.8 mmol) and the mixture stirred for 10 min. Chloromethyl methyl ether (0.82 ml, 10.8 mmol) was then added and stirring was continued for 16 h, gradually allowing the mixture to reach room temperature. The reaction was quenched with $H_2O$ (15 ml) and extracted with $CH_2Cl_2$ (3×20 ml). The combined organic layers were washed with $H_2O$ (20 ml), brine (20 ml), dried over $Na_2SO_4$ and the solvent evaporated under reduced pressure. The residue was purified by column chromatography with ethyl acetate-hexane (3%) to give compound 2 (6.2 g, 99%) as a colorless oil, Rf: 0.63 (10% EtOAc/Hexane). IR (ATR, cm$^{-1}$): 2932, 2868, 2853, 1646, 1472, 1369, 1120, 1009, 625. $^1$H-NMR ($CDCl_3$, δ): 6.31 (1H, dd, J=6.0/1.8 Hz, H-1), 4.93 (1H, d, J=6.6 Hz, $CH_2$-MOM), 4.78 (1H, d, J=6.6 Hz, $CH_2$-MOM), 4.75 (1H, dd, J=6.1 Hz, J=2.0 Hz, H-2), 4.32 (1H, d, J=7.4 Hz, H-3), 4.19 (1H, dd, J=10.4/4.9 Hz, H-6), 4.12 (1H, dd, J=10.3/7.4 Hz, H-6), 4.00 (1H, t, H-4), 3.88 (1H, m, H-5), 3.45 (3H, s, $CH_3$-MOM), 1.09 (9H, s, $CH_3$-$^t$Bu), 1.02 (9H, s, $CH_s$-$^t$Bu) ppm. $^{13}$C-NMR ($CDCl_3$, δ): 144.1 (CH-1), 102.1 (CH-2), 95.6 ($CH_2$-MOM), 76.0 (CH-4), 74.1 (CH-3), 72.9 (CH-5), 65.9 ($CH_2$-6), 55.3 ($CH_3$-MOM), 27.4 ($CH_3$-$^t$Bu), 26.9 ($CH_3$-$^t$Bu), 22.7 (C-$^t$Bu), 19.9 (C-$^t$Bu) ppm. MS(ESI) [m/z, (%)]: 269.15 (M$^+$-MOM, 100), 345.17 (M$^+$+Na, 7). HRMS (ESI): 353.1755 calculated for $C_{16}H_{30}NaO_5Si$; found 353.1756.

Synthesis of (4R,5R)-2,2-di-tert-butyl-4-((R)-1-(methoxymethoxy)allyl)-1,3,2-dioxasilinan-5-ol (3)

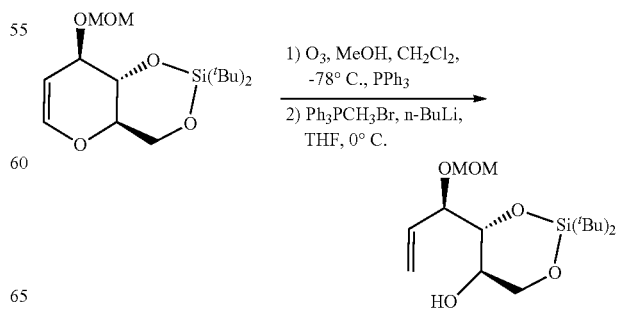

To a solution of compound 2 (807 mg, 2.43 mmol) in CH$_2$Cl$_2$ (65 ml) and MeOH (20 ml), a current of O$_3$ (1.0 ml/min, 0.40 A) was passed for 10 min. The O$_3$ flux was stopped when the color of the mixture changed to blue, which means a saturated solution of O$_3$. After passing a flow of Ar, PPh$_3$ (764 mg, 2.91 mmol) was added in small portions, and after 5 min under stirring a saturated solution of NH$_4$Cl (15 ml) was added and the mixture was extracted with CH$_2$Cl$_2$ (2×30 ml). The combined organic layers was dried over Na$_2$SO$_4$ and the solvent evaporated under reduced pressure to provide a crude product.

To a suspension of methyltriphenylphosphonium bromide (3.47 mg, 9.72 mmol) in THF (10 mL) at 0° C. was added n-BuLi 2.5 M solution in hexane (3.4 ml, 8.5 mmol) and stirring was continued for 1 h. A solution of previous crude in THF (5 ml) was added and the mixture stirred for 4 h, then quenched with an aqueous saturated solution of NH$_4$Cl (10 ml) and the product extracted with EtOAc (3×15mL). The combined organic phases were dried, filtered and evaporated to give a residue which was chromatographed on silica gel using ethylacetate-hexane (5%) to give compound 3 (646 mg, 80%) as a colorless oil, Rf: 0.37 (20% EtOAc/Hexane). IR (ATR, cm$^{-1}$): 3442, 2960, 2931, 2858, 1474, 1070, 826, 652. $^1$H-NMR (CDCl$_3$, δ): 6.01 (1H, m, H-2), 5.37 (2H, m, H-1), 4.68 (2H, m, CH$_2$-MOM), 4.35 (1H, d, J=6.9 Hz, H-3), 4.14 (1H, m), 3.96 (2H, m), 3.83 (1H, m), 3.44 (1H, m, CH$_3$-MOM), 1.05 (9H, s, CH$_3$-$^t$Bu), 1.00 (9H, s, CH$_3$-$^t$Bu) ppm. $^{13}$C-NMR (CDCl$_3$, δ): 134.0 (CH-2), 118.5 (CH$_2$-1), 95.1 (CH$_2$-MOM), 79.6 (CH), 78.6 (CH), 68.2 (CH$_2$-6), 67.1 (CH), 55.9 (CH$_3$-MOM), 27.5 (CH$_3$-$^t$Bu), 27.0 (CH$_3$-$^t$Bu), 22.8 (C-$^t$Bu), 20.2 (C-$^t$Bu) ppm. MS(ESI) [m/z, (%)]: 271.17 (M$^+$-OMOM, 100), 355.19 (M$^+$+Na, 9). HRMS (ESI): 355.1911 calculated for C$_{16}$H$_{32}$NaO$_5$Si; found 355.1906.

Synthesis of (4S,5R)-2,2-di-tert-butyl-5-(methoxymethoxy)-4-((R)-1-(methoxymethoxy)allyl)-1,3,2-dioxasilinane (4)

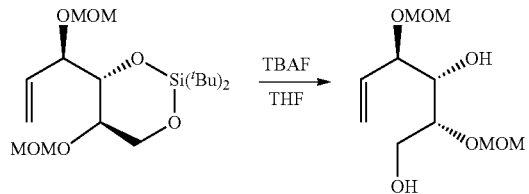

DIPEA (1.6 ml, 9.2 mmol) was added dropwise to a solution of 3 (613 mg, 1.84 mmol) in CH$_2$Cl$_2$ (10 ml) cooled to 0° C., and the mixture stirred for 10 min. Chloromethyl methyl ether (0.7 ml, 9.2 mmol) was then added and stirring was continued for 16 h, gradually allowing the mixture to reach room temperature. The reaction was quenched with H$_2$O (15 ml) and extracted with CH$_2$Cl$_2$ (3×20 ml). The combined organic layers were washed with H$_2$O (20 mL), brine (20 mL), dried over Na$_2$SO$_4$ and the solvent evaporated under reduced pressure. The residue was purified by column chromatography with ethyl acetate-hexane (5%) to give compound 4 (681 mg, 99%) as a colorless oil, Rf: 0.40 (10% EtOAc/Hexane). IR (ATR, cm$^{-1}$): 2958, 2931, 2857, 1473, 1142, 1045, 826. $^1$H-NMR (CDCl$_3$, δ): 6.02 (1H, m, H-2), 5.30 (2H, m, H-1), 4.75 (2H, d, J=20.1/6.7 Hz, CH$_2$-MOM), 4.62 (2H, d, J=20.7/6.7 Hz, CH$_2$-MOM), 4.21 (2H, m, H-3), 3.88 (3H, m), 3.39 (3H, s, CH$_3$-MOM), 3.37 (3H, s, CH$_3$-MOM), 1.04 (9H, s, CH$_3$-$^t$Bu), 1.03 (9H, s, CH$_3$-$^t$Bu) ppm. $^{13}$C-NMR (CDCl$_3$, δ): 135.9 (CH-2), 118.2 (CH$_2$-1), 97.2 (CH$_2$-MOM), 94.4 (CH$_2$-MOM), 79.9 (CH), 77.7 (CH), 73.5 (CH), 66.9 (CH$_2$-6), 55.8 (CH$_3$-MOM), 55.7 (CH$_3$-MOM), 27.5 (CH$_3$-$^t$Bu), 26.9 (CH$_3$-$^t$Bu), 22.7 (C-$^t$Bu), 20.5 (C-$^t$Bu) ppm. MS(ESI) [m/z, (%)]: 253.16 (100), 338.34 (30), 399.21 (M$^+$+Na, 85). HRMS (ESI): 399.2173 calculated for C$_{18}$H$_{36}$NaO$_6$Si; found 399.2161.

Synthesis of (2R,3S,4R)-2,4-bis(methoxymethoxy)hex-5-ene-1,3-diol (5)

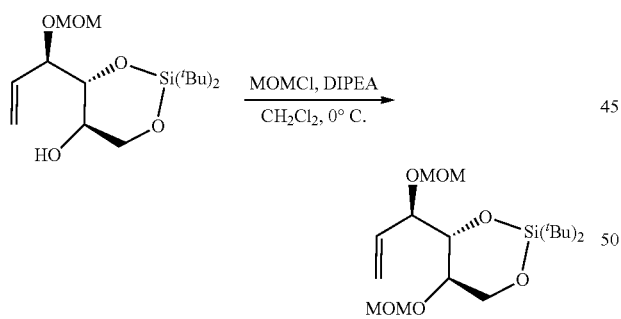

To a solution of 4 (1.25 g, 3.32 mmol) in THF (6 mL) was added a 1.0 M solution of TBAF (9.96 mL, 9.96 mmol) at room temperature and the mixture was stirred for 16 h in the same conditions. The solvent was evaporated and the residue was chromatographed on silica gel using ethyl acetate-hexane (80%) as eluent affording compound 5 (776 mg, 99%) as a colorless oil, Rf: 0.78 (50% EtOAc/Hexane). IR (ATR, cm$^{-1}$): 3436, 2950, 2924, 2853, 1143, 1028, 918. $^1$H-NMR (CDCl$_3$, δ): 5.83 (1H, m, H-2), 5.33 (2H, m, H-1), 4.73 (3H, m, CH$_2$-MOM), 4.59 (1H, m, CH$_2$-MOM), 4.21 (1H, m), 3.81 (2H, m), 3.65 (2H, m), 3.43 (3H, s, CH$_3$-MOM), 3.39 (3H, s, CH$_3$-MOM), 3.24 (1H, s, OH), 2.92 (1H, s, OH) ppm. $^{13}$C-NMR (CDCl$_3$, δ): 134.8 (CH-2), 119.6 (CH$_2$-1), 97.1 (CH$_2$-MOM), 94.2 (CH$_2$-MOM), 80.4 (CH), 77.0 (CH), 74.1 (CH), 62.8 (CH$_2$-6), 56.0 (CH$_3$-MOM), 55.9 (CH$_3$-MOM) ppm. MS(ESI) [m/z, (%)]: 143.07 (60), 237.13 (M$^+$+1, 10), 259.11 (M$^+$+Na, 100). HRMS (ESI): 237.1333 calculated for C$_{10}$H$_{21}$O$_6$; found 237.1333.

Synthesis of (5S,6S,7R)-5-(iodomethyl)-7-vinyl-2,4,8,10-tetraoxaundecan-6-ol (6)

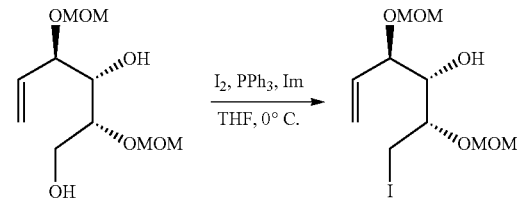

To a solution of diol 5 (364 mg, 1.54 mmol) in THF (10 mL) at room temperature were added sequentially PPh$_3$ (605 mg, 2.31 mmol) and imidazole (314 mg, 4.62 mmol). After cooling the mixture to 0° C., I$_2$ (545 mg, 2.15 mmol) was added and stirring continued for 5 h. The reaction was quenched with an aqueous saturated solution of NaHCO$_3$ (10 mL) and the product extracted with EtOAc (3×20 ml). The organic phase was washed with a 10% aqueous solution of Na$_2$S$_2$O$_3$ (10 mL) and brine (10 mL), dried over Na$_2$SO$_4$, filtered and concentrated to give a residue which was chromatographed on silica gel using ethylacetate-hexane (30%) as eluent affording compound 6 (465 mg, 87%) as a colorless oil, Rf: 0.55 (50% EtOAc/Hexane). IR (ATR, cm$^{-1}$): 3451, 2923, 2853, 1464, 1050, 1028, 919. $^1$H-NMR (CDCl$_3$, δ): 5.88 (1H, m, H-2), 5.35 (2H, m, H-1), 4.74 (3H, m, CH$_2$-MOM), 4.60 (1H, m, CH$_2$-MOM), 4.28 (1H, m), 3.59 (2H, m), 3.47 (3H, s, CH$_3$-MOM), 3.40 (3H, s, CH$_3$-MOM), 3.34 (1H, m), 2.51 (1H, s, OH) ppm. $^{13}$C-NMR (CDCl$_3$, δ): 134.8 (CH-2), 119.5 (CH$_2$-1), 97.0 (CH$_2$-MOM), 94.3 (CH$_2$-MOM), 76.3 (CH), 76.2 (CH), 75.3 (CH), 56.7 (CH$_3$-MOM), 56.1 (CH$_3$-MOM), 10.2 (CH$_2$-6) ppm. MS(ESI) [m/z, (%)]: 369.0169 (M$^+$+Na, 100). HRMS (ESI): 369.0169 calculated for C$_{10}$H$_{19}$INaO$_5$; found 369.0165.

Synthesis of (5R,6S)-8,8-diethyl-6-((S)-2-iodo-1-(methoxymethoxy)ethyl)-5-vinyl-2,4,7-trioxa-8-siladecane (7)

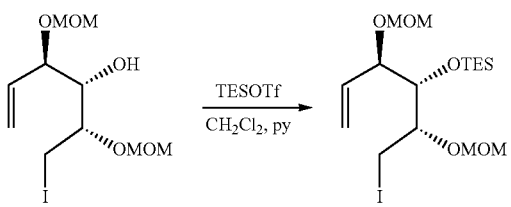

To a solution of compound 6 (1.31 g, 3.8 mmol) in CH$_2$Cl$_2$ (30 mL) were added pyridine (3.1 ml g, 38 mmol) and TESOTf (1.72 ml, 7.6 mmol) and the mixture was stirred for 1 h at room temperature. After that time, a saturated solution of NaHCO$_3$ (10 mL) was added and the product extracted with EtOAc (2×20 mL). The organic layer was washed with Cu$_2$SO$_4$ (2×10 ml) and dried over Na$_2$SO$_4$, filtered and the solvent evaporated under reduced pressure. The residue was purified by column chromatography with ethyl acetate-hexane (5%) to give compound 7 (1.73 g, 99%) as a colorless oil, Rf: 0.55 (10% EtOAc/Hexane). IR (ATR, cm$^{-1}$): 2953, 2877, 1458, 1143, 1033, 921, 742. $^1$H-NMR (CDCl$_3$, δ): 5.82 (1H, m, H-2), 5.33 (2H, m, H-1), 4.69 (4H, m, CH$_2$-MOM), 4.11 (1H, m), 3.90 (1H, m), 3.69 (1H, m), 3.52 (1H, m), 3.48 (3H, s, CH$_3$-MOM), 3.38 (3H, s, CH$_3$-MOM), 3.31 (1H, m), 0.97 (9H, m, CH$_3$-TES), 0.70 (4H, m, CH$_2$-TES), 0.53 (2H, m, CH$_2$-TES) ppm. $^{13}$C-NMR (CDCl$_3$, δ): 135.2 (CH-2), 118.7 (CH$_2$-1), 96.8 (CH$_2$-MOM), 94.6 (CH$_2$-MOM), 78.5 (CH), 78.4 (CH), 76.9 (CH), 56.7 (CH$_3$-MOM), 55.8 (CH$_3$-MOM), 8.8 (CH$_2$-6), 6.9 (CH$_3$-TES), 6.8 (CH$_3$-TES), 6.4 (CH$_2$-TES), 5.3 (CH$_2$-TES) ppm. MS(ESI) [m/z, (%)]: 337.04 (42), 483.10 (M$^+$+Na, 100). HRMS (ESI): 483.1034 calculated for C$_{16}$H$_{33}$INaO$_5$Si; found 483.1019.

Synthesis of (3R,4R,5R)-3,5-bis(methoxymethoxy)-4-((triethylsilyl)oxy)hept-6-enenitrile (8)

To a solution of 7 (150 mg, 0.32 mmol) in DMSO (2 mL) was added NaCN (32 mg, 0.64 mmol). The mixture was stirred at rt for 14 h. The reaction was quenched with H$_2$O (6 ml), extracted with EtOAc (10 mL) and the organic layer washed with H$_2$O (2×10 mL) and brine (2×10 ml). After drying with Na$_2$SO$_4$ and solvent evaporation the residue was purified by column chromatography with ethyl acetate-hexane (10%) to give compound 8 (76 mg, 64%) as a colorless oil, Rf: 0.50 (10% EtOAc/Hexane). IR (ATR, cm$^{-1}$): 2853, 2878, 2251, 1150, 1100, 1003, 919, 740. $^1$H-NMR (CDCl$_3$, δ): 5.76 (1H, m, H-2), 5.32 (2H, m, H-1), 4.66 (4H, m, CH$_2$-MOM), 3.98 (3H, m), 3.45 (3H, s, CH$_3$-MOM), 3.36 (3H, s, CH$_3$-MOM), 2.67 (2H, m, CH$_2$-6), 0.97 (9H, m, CH$_3$-TES), 0.66 (6H, m, CH$_2$-TES) ppm. $^{13}$C-NMR (CDCl$_3$, δ): 134.4 (CH-2), 119.0 (CH$_2$-1), 118.7 (C-7), 95.9 (CH$_2$-MOM), 94.5 (CH$_2$-MOM), 78.1 (CH), 75.4 (CH), 73.7 (CH), 56.2 (CH$_3$-MOM), 55.7 (CH$_3$-MOM), 19.9 (CH$_2$-6), 6.8 (CH$_3$-TES), 4.9 (CH$_2$-TES) ppm. MS(ESI) [m/z, (%)]: 360.22 (M$^+$+1, 48), 474.30 (100). HRMS (ESI): 360.2200 calculated for C$_{17}$H$_{34}$NO$_5$Si; found 360.2193.

Synthesis of (3R,4R,5R)-3,5-bis(methoxymethoxy)-4-((triethylsilyl)oxy)hept-6-enal (9)

To a solution of 8 (123 mg, 0.34 mmol) in CH$_2$Cl$_2$ (3 ml) cooled to −78° C. was added a solution 1 M of DIBAL-H in Hexane (0.38 ml, 0.38 mmol) and was stirred for 20 min.
Over the solution were added a few drops of MeOH (5 ml) and a saturated solution of NH$_4$Cl (1 ml) and extracted with CH$_2$Cl$_2$ (2×10 ml). After drying with Na$_2$SO$_4$ and solvent evaporation the residue was purified by column chromatography with ethyl acetate-hexane (8%) to give compound 9 (103 mg, 83%) as a colorless oil, Rf: 0.52 (20% EtOAc/Hexane). IR (ATR, cm$^{-1}$): 2953, 2878, 1726, 1150, 1099, 1029, 741. $^1$H-NMR (CDCl$_3$, δ): 9.80 (1H, s, H-7), 5.77 (1H, m, H-2), 5.31 (2H, m, H-1), 4.67 (4H, m, MOM), 4.22 (1H, m), 3.98 (3H, m), 3.37 (3H, s, CH$_3$-MOM), 3.34 (3H, s, CH$_3$-MOM), 2.64 (2H, m, CH$_2$-6), 0.97 (9H, t, J=7.9 Hz, CH$_3$-TES), 0.65 (6H, q, J=7.9 Hz, CH$_2$-TES) ppm. $^{13}$C-NMR (CDCl$_3$, δ): 201.6 (CH-7), 134.6 (CH-2), 118.8 (CH$_2$-

1), 95.7 (CH$_2$-MOM), 94.5 (CH$_2$-MOM), 78.6 (CH), 76.3 (CH), 73.6 (CH), 55.8 (CH$_3$-MOM), 55.6 (CH$_3$-MOM), 44.8 (CH$_2$-6), 6.8 (CH$_3$-TES), 5.0 (CH$_2$-TES) ppm. MS(ESI) [m/z, (%)]: 385.20 (M$^+$+Na, 100). HRMS (ESI): 385.2017 calculated for C$_{17}$H$_{34}$NaO$_6$Si; found 385.2006.

Synthesis of (5R,6R)-6-((R)-4,4-dibromo-1-(methoxymethoxy)but-3-en-1-yl)-8,8-diethyl-5-vinyl-2,4,7-trioxa-8-siladecane (10)

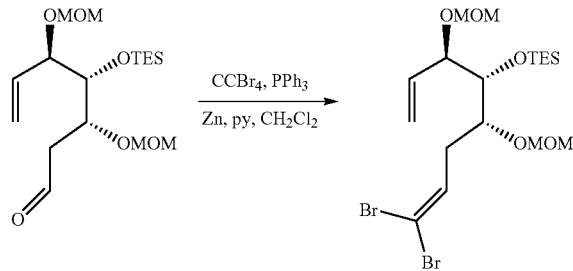

To a suspension of Zn (78 mg, 1.2 mmol) in CH$_2$Cl$_2$ (5 ml) were added sequentially CBr$_4$ (398 mg, 1.2 mmol) and PPh$_3$ (317 mg, 1.2 mmol) and the mixture was stirred for 1h at rt. After that, compound 9 (87 mg, 0.24 mmol) and pyridine (195 µL, 2.4 mmol) in CH$_2$Cl$_2$ (1 ml) were added and the mixture was kept at the same conditions for 2 h. Et$_2$O (15 ml) was added and the suspension concentrated. The residue was purified by column chromatography with ethyl acetate-hexane (10%) to give compound 10 (97 mg, 78%) as a colorless oil, Rf: 0.75 (20% EtOAc/Hexane). IR (ATR, cm$^{-1}$): 2953, 2878, 1726, 1150, 1099, 1029, 741. $^1$H-NMR (CDCl$_3$, δ): 6.56 (1H, t, J=7.1 Hz, H-7), 5.77 (1H, m, H-2), 5.33 (2H, m, H-1), 4.70 (2H, dd, J=6.8/5.2 Hz, CH$_2$-MOM), 4.61 (1H, d, J=6.8 Hz, CH$_2$-MOM), 4.58 (1H, d, J=6.8 Hz, CH$_2$-MOM), 3.98 (1H, m), 3.88 (1H, m), 3.75 (1H), 3.41 (3H, s, CH$_3$-MOM), 3.39 (3H, s, CH$_3$-MOM), 2.40 (2H, m, CH$_2$-6), 1.00 (9H, t, J=7.9 Hz, CH$_3$-TES), 0.68 (6H, q, J=7.9 Hz, CH$_2$-TES) ppm. $^{13}$C-NMR (CDCl$_3$, δ): 136.7 (CH-7), 134.7 (CH-2), 119.0 (CH$_2$-1), 95.3 (CH$_2$-MOM), 94.5 (CH$_2$-MOM), 89.1 (C-8), 78.8 (CH), 76.3 (CH), 75.9 (CH), 55.8 (CH$_3$-MOM), 55.6 (CH$_3$-MOM), 33.8 (CH$_2$-6), 6.9 (CH$_3$-TES), 5.1 (CH$_2$-TES) ppm. MS(ESI) [m/z, (%)]: 539.04 (M$^+$+Na, 50), 541.04 (M$^+$+Na, 100), 543.03 (M$^+$+Na, 50). HRMS (ESI): 541.0415 calculated for C$_{18}$H$_{34}$Br$_2$NaO$_5$Si; found 541.0398.

Synthesis (in Two Steps) of (5R,6R)-6-((R)-4,4-dibromo-1-(methoxymethoxy)but-3-en-1-yl)-8,8-diethyl-5-vinyl-2,4,7-trioxa-8-siladecane (10)

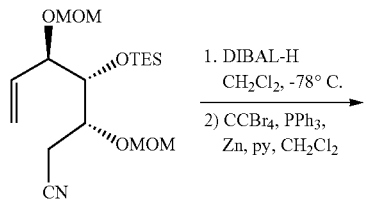

1. DIBAL-H
CH$_2$Cl$_2$, -78° C.

2) CCBr$_4$, PPh$_3$,
Zn, py, CH$_2$Cl$_2$

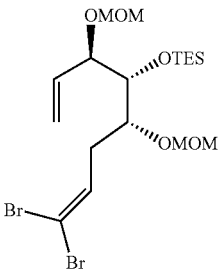

To a solution of 8 (500 mg, 1.39 mmol) in CH$_2$Cl$_2$ (12 ml) cooled to −78° C. was added a solution 1 M of DIBAL-H in Hexane (1.53 ml, 1.53 mmol) and was stirred for 7 min.

Over the solution was added dropwise MeOH (10 ml) and a saturated solution of NH$_4$Cl (5 ml) and extracted with CH$_2$Cl$_2$ (2×10 ml). After drying with Na$_2$SO$_4$ the solvent was concentrated. To a suspension of Zn (454 mg, 6.95 mmol) in CH$_2$Cl$_2$ (18 ml) were added sequentially CBr$_4$ (2.3 g, 6.95 mmol) and PPh$_3$ (1.8 g, 6.95 mmol) and the mixture was stirred for 1 h at rt. After that, previous crude and pyridine (1.11 mL, 13.9 mmol) in CH$_2$Cl$_2$ (5 ml) were added and the mixture was kept at the same conditions for 2 h. Et$_2$O (40 ml) was added and the suspension concentrated. The residue was purified by column chromatography with ethyl acetate-hexane (10%) to give compound 10 (502 mg, 70%).

Synthesis of (5R,6R)-8,8-diethyl-6-((R)-1-(methoxymethoxy)allyl)-5-(prop-2-yn-1-yl)-2,4,7-trioxa-8-siladecane (11)

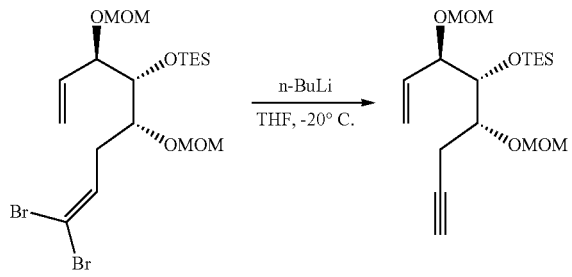

To a solution of compound 10 (151 mg, 0.29 mmol) in THF (5 ml) at −78° C. was added dropwise n-BuLi 2.5 M in hexane (174 µl, 0.43 mmol) and the mixture left stirring at this temperature for 10 min till brown color. After that time, an aqueous saturated solution of NH$_4$Cl (5 ml) was added and the product extracted with EtOAc (3×10 mL). The combined organic phases were dried over Na$_2$SO$_4$, filtered and evaporated to give a residue which was chromatographed with ethylacetate-hexane (3%) to give compound 11 (101 mg, 99%) as a colorless oil, Rf: 0.52 (10% EtOAc/Hexane). IR (ATR, cm$^{-1}$): 3310, 2952, 2877, 1441, 1030, 919, 740. $^1$H-NMR (CDCl$_3$, δ): 5.83 (1H, m, H-2), 5.33 (2H, m, H-1), 4.76 (2H, d, J=1.3 Hz, CH$_2$-MOM), 4.66 (2H, m, CH$_2$-MOM), 4.11 (1H, m), 3.91 (2H, m), 3.45 (3H, s, CH$_3$-MOM), 3.39 (3H, s, CH$_3$-MOM), 2.57 (2H, m, CH$_2$-6), 1.99 (1H, s, H-8), 1.00 (9H, m, CH$_3$-TES), 0.66 (6H, m, CH$_2$-TES) ppm. $^{13}$C-NMR (CDCl$_3$, δ): 135.3 (CH-2), 118.8 (CH$_2$-1), 96.3 (CH$_2$-MOM), 94.6 (CH$_2$-MOM), 82.3 (C-7), 78.5 (CH), 76.4 (CH), 76.0 (CH), 69.6 (CH-8), 55.9 (CH$_3$-MOM), 55.7 (CH$_3$-MOM), 20.8 (CH$_2$-6), 6.9 (CH$_3$-TES), 5.1 (CH$_2$-TES) ppm. MS(ESI) [m/z, (%)]: 381.20 (M$^+$+Na, 100). HRMS (ESI): 381.2068 calculated for C$_{18}$H$_{34}$NaO$_5$Si; found 381.2059.

Synthesis of ((3-(methoxymethoxy)propoxy)methyl)benzene (13)

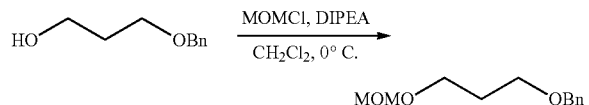

To a solution of alcohol 12 (5 g, 30 mmol) in CH$_2$Cl$_2$ (30 mL) and cooled to 0° C., DIPEA (10.5 mL, 60 mmol) was added dropwise and the mixture was stirred for 10 min. Chloromethyl methyl ether (4.6 mL, 60 mmol) was then added and stirring continued for 2 h, gradually allowing the mixture to reach rt. The reaction was quenched with H$_2$O (20 mL) and extracted with CH$_2$Cl$_2$ (3×20mL). The combined organic layers were washed with brine (20 mL), dried over Na$_2$SO$_4$ and the solvent evaporated under reduced pressure. The residue was chromatographed on silica gel using EtOAc/Hexane (10%) as eluent affording 13 (6.04 g, 96%) as a colorless oil; Rf: 0.76 (20% EtOAc/Hexane). IR (ATR, cm$^{-1}$): 2928, 2875, 1453, 1102, 1038, 918, 735, 696. $^1$H-NMR (CDCl$_3$, δ): 7.37 (5H, m, Ph), 4.64 (2H, s, CH$_2$-Bn), 4.54 (2H, s, CH$_2$-MOM), 3.68 (2H, t, J=6.4 Hz, CH$_2$-1/3), 3.62 (2H, t, J=6.3 Hz, CH$_2$-1/3), 3.38 (3H, s, CH$_3$-MOM), 1.95 (2H, m, CH$_2$-2) ppm. $^{13}$C-NMR (CDCl$_3$, δ): 138.6 (C-Ph), 128.4 (CH-Ph), 127.6 (CH-Ph), 96.5 (CH$_2$-MOM), 73.0 (CH$_2$-Bn), 67.3 (CH$_2$-1/3), 64.8 (CH$_2$-1/3), 55.1 (CH$_3$-MOM), 30.2 (CH$_2$-2) ppm. MS (ESI) [m/z, (%)]: 179.10 (100), 211.13 ([M+1]$^+$,27), 233.11 ([M+Na]$^+$, 63). HRMS (ESI): 211.1329 calculated for C$_{12}$H$_{19}$O$_3$ and found 211.1328.

Synthesis of 3-(methoxymethoxy)propyl methanesulfonate (14)

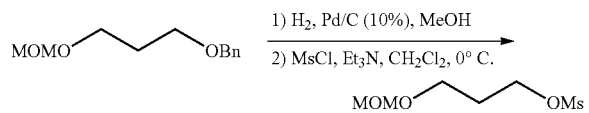

To a solution of compound 13 (6.04 g, 28.7 mmol) in MeOH (40 mL) was added a catalytic amount of Pd/C (10%) and the suspension was stirred for 24 h at room temperature under H$_2$. The mixture was then filtered through celite and the filtrate was rotatory evaporated to afford a residue. To a solution of the previous residue in CH$_2$Cl$_2$ (40 mL) at 0° C. were added Et$_3$N (12.0 mL, 86.1 mmol), a catalytic amount of DMAP and MsCl (6.7 mL, 86.1 mmol). After stirring the mixture at this temperature for 3 h, H$_2$O (20 ml) was added and the product was extracted with CH$_2$Cl$_2$ (3×15 mL). The combined organic phases were dried over Na$_2$SO$_4$, filtered and concentrated to give a residue which was chromatographed on silica gel using EtOAc/Hexane (35%) as eluent, affording mesylate 14 (5.67 g, 99%) as a colorless oil; Rf: 0.52 (50% EtOAc/Hexane). IR (ATR, cm$^{-1}$): 3556, 2937, 2886, 1347, 1169, 1040, 942. $^1$H-NMR (CDCl$_3$, δ): 4.50 (2H, s, CH$_2$-MOM), 4.23 (2H, t, J=6.3 Hz, CH$_2$-1), 3.52 (2H, t, J=6.0 Hz, CH$_2$-3), 3.24 (3H, s, CH$_3$-MOM), 2.92 (3H, s, CH$_3$-Ms), 1.91 (2H, m, CH$_2$-2) ppm. $^{13}$C-NMR (CDCl$_3$, δ): 96.4 (CH$_2$-MOM), 67.3 (CH$_2$-1), 63.0 (CH$_2$-3), 55.1 (CH$_3$-MOM), 36.9 (CH$_3$-Ms), 29.3 (CH$_2$-2) ppm. MS (ESI) [m/z, (%)]: 155.04 (100), 167.04 (60), ([M+1]+, 10). HRMS (ESI): 199.0635 calculated for C$_6$H$_{15}$O$_5$S and found 199.0638. Synthesis of (5R,6R)-6-((R)-1-(methoxymethoxy)allyl)-5-(prop-2-yn-1-yl)-2,4,7,11,13-pentaoxatetradecane (15)

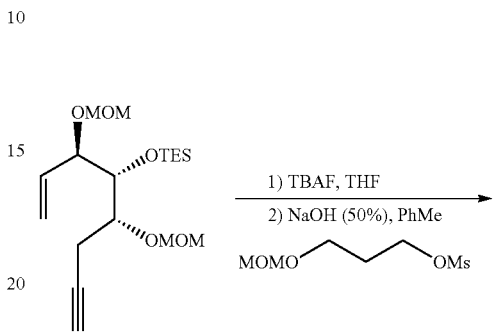

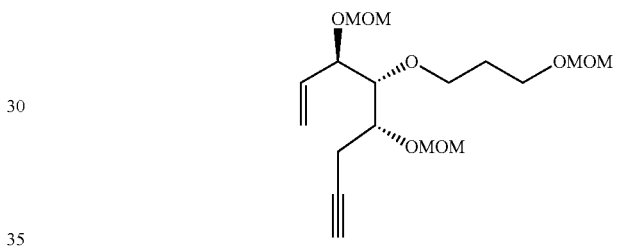

To a flask with compound 11 (0.45 g, 1.26 mmol) was added a solution of TBAF 1.0 M in THF (3.76 mL, 3.76 mmol) and the mixture stirred for 1 h. Then to the mixture were added the mesylate 14 (1.25 g, 6.30 mmol) in PhMe (20 mL) and a 50% aqueous NaOH solution (10 mL) and it was vigorously stirred for 6 days at rt. After that time, the product was extracted with EtOAc (3×20 mL). The combined organic phases were dried, filtered and evaporated to give a residue which was chromatographed on silica gel using EtOAc/Hexane (20%) as eluent, affording compound 15 (0.44 g, 90%) as a colorless liquid; Rf: 0.50 (30% EtOAc/Hexane). IR (ATR, cm$^{-1}$): 3273, 2925, 2889, 1151, 1102, 1034, 918. $^1$H-NMR (CDCl$_3$, δ): 5.89 (1H, m, H-2), 5.32 (2H, m, H-1), 4.74 (4H, m, CH$_2$-MOM), 4.62 (2H, s, CH$_2$-MOM), 4.25 (1H, m, H-4), 3.88 (1H, m), 3.82 (1H, m), 3.75 (1H, m), 3.62 (2H, m), 3.52 (1H, m), 3.45 (3H, s, CH$_3$-MOM), 3.39 (3H, s, CH$_3$-MOM), 3.36 (3H, s, CH$_3$-MOM), 2.66 (2H, m, H-6), 2.02 (1H, m, H-8), 1.90 (2H, m, H-10) ppm. $^{13}$C-NMR (CDCl$_3$, δ): 135.7 (CH-2), 118.7 (CH-1), 97.0 (CH$_2$-MOM), 96.5 (CH$_2$-MOM), 94.5 (CH$_2$-MOM), 82.7 (CH-4), 81.6 (C-7), 77.4 (CH), 76.2 (CH), 70.5 (CH$_2$), 70.1 (CH-8), 64.9 (CH$_2$), 56.0 (CH$_3$-MOM), 55.9 (CH$_3$-MOM), 55.2 (CH$_2$-MOM), 30.5 (CH$_2$-10), 21.2 (CH$_2$-6) ppm. MS (ESI) [m/z, (%)]: 239.12 (55), 369.18 ([M+Na]$^+$, 100). HRMS (ESI): 369.1883 calculated for C$_{17}$H$_{30}$NaO$_7$ and found 369.1873.

Synthesis of (1R,2R,3R,Z)-5-(2-((1R,3aS,7aR,E)-1-((R)-6-hydroxy-6-methylheptan-2-yl)-7a-methyloctahydro-4H-inden-4-ylidene)ethylidene)-2-(3-hydroxypropoxy)-4-methylenecyclohexane-1,3-diol (Eldecalcitol)

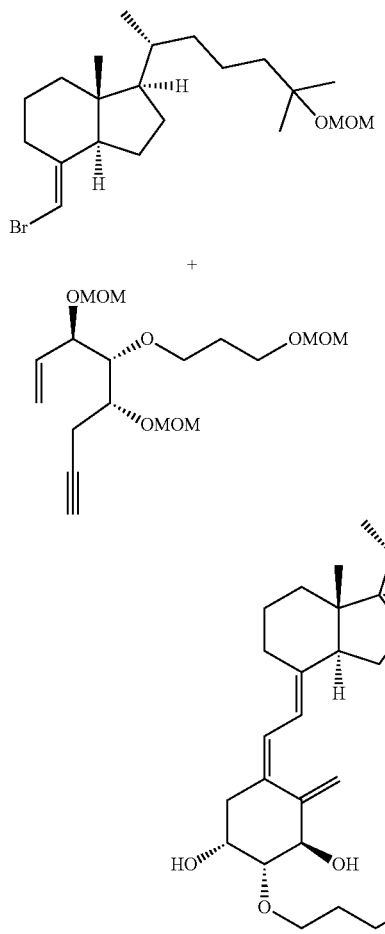

The enyne 15 (55 mg, 0.11 mmol) and vinyl bromide 16 (69 mg, 0.17 mmol) were dissolved in Et$_3$N/PhMe (1:1, 4 mL), and Pd(PPh$_3$)$_4$ was added in catalytic amount. The resulting yellow solution was stirred at 110° C. for 2 h. The reaction mixture was quenched with Et$_2$O (5 mL) and the solvent evaporated to afford a residue. To a solution of the latter in MeOH (4 mL) was added CSA (191 mg, 0.82 mmol) and the mixture stirred at rt for 3 days. The residue was filtered and the resulting solid purified by column chromatography with MeOH/CH$_2$Cl$_2$ (5%) as eluent, affording compound Eldecalcitol (19 mg, 36%) as a colorless oil; Rf: 0.33 (EtOAc). $^1$H-NMR (CDCl$_3$, δ): 6.36 (1H, dd, J=11.2/1.7 Hz, H-6), 6.05 (1H, d, J=11.2 Hz, H-7), 5.51 (1H, t, J=2.2 Hz, H-19), 5.08 (1H, t, J=2.2 Hz, H-19), 4.32 (1H, d, J=9.1 Hz, H-1), 4.27 (1H, d, J=3.3 Hz, H-3), 3.92 (2H, m, CH$_2$-3'), 3.72 (2H, m, CH$_2$-1'), 3.26 (1H, dd, J=9.0/12.8 Hz, H-2), 2.82 (1H, dd, J=12.0/4.1 Hz), 2.54 (1H, dd, J=14.5/3.9 Hz), 2.42 (1H, d, J=14.3 Hz), 1.99 (2H, m), 1.86 (3H, m), 1.67 (2H, m, CH$_2$-2'), 1.43 (8H, m), 1.28 (4H, m), 1.22 (6H, s, CH$_3$-26/27), 0.94 (3H, d, J=6.4 Hz, CH$_3$-21), 0.87 (m, 1H), 0.55 (3H, s, CH$_3$-18) ppm. $^{13}$C-NMR (CDCl$_3$, δ): 144.3 (C-10), 142.9 (C-8), 132.3 (C-5), 124.8 (CH-6), 117.2 (CH-7), 111.8 (CH$_2$-19), 85.4 (CH-2), 71.4 (CH-1), 71.2 (C-25), 68.2 (CH$_2$-1'), 66.5 (CH-3), 61.9 (CH$_2$-3'), 56.5 (CH), 56.4 (CH), 45.9 (C-13), 44.4 (CH$_2$), 40.5 (CH$_2$), 36.4 (CH$_2$), 36.1 (CH-20), 34.0 (CH$_2$), 31.8 (CH$_2$-2'), 29.3 (CH$_3$-26/27), 29.2 (CH$_3$-26/27), 29.1 (CH$_2$), 27.7 (CH$_2$), 23.7 (CH$_2$), 22.3 (CH$_2$), 20.8 (CH$_2$), 18.8 (CH$_3$-21), 11.9 (CH$_3$-18) ppm.

Synthesis of (1R,2R,6R,Z)-2,6-bis(methoxymethoxy)-4-(2-((1R,3aS,7aR,E)-1-((R)-6-(methoxymethoxy)-6-methylheptan-2-yl)-7a-methyloctahydro-4H-inden-4-ylidene)ethylidene)-3-methylenecyclohexan-1-ol (17)

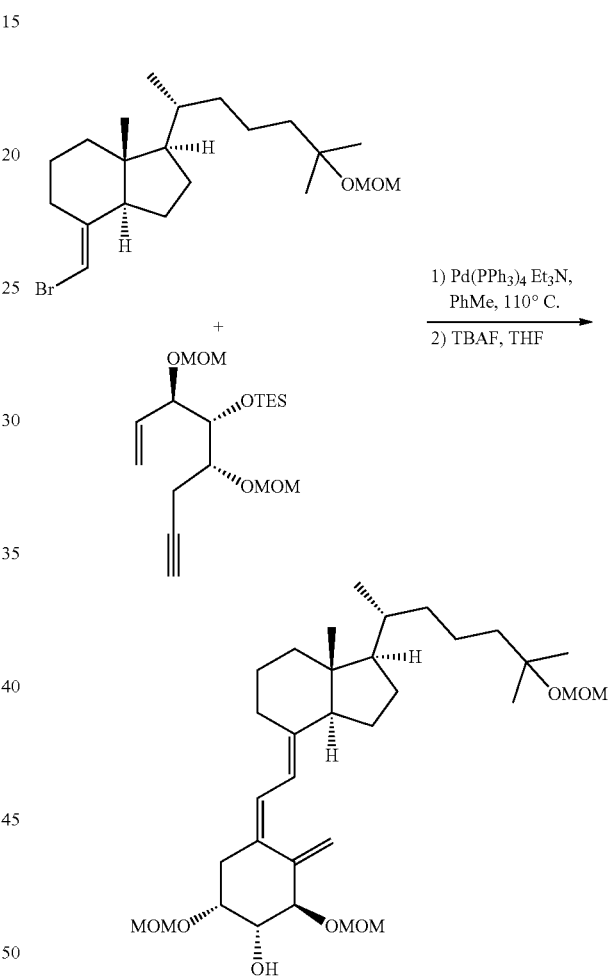

The enyne 11 (137 mg, 0.38 mmol) and vinyl bromide 16 (230 mg, 0.57 mmol) were dissolved in Et$_3$N/PhMe (1:1, 12 mL), and Pd(PPh$_3$)$_4$ was added in catalytic amount. The resulting yellow solution was stirred at 110° C. for 3 h. The reaction mixture was quenched with Et$_2$O (5 mL) and the solvent evaporated to afford a residue which was taken up in THF (4 mL). A solution of TBAF 1.0 M in THF (1.14 mL, 1.14 mmol) was then added and the mixture stirred for 20 h. After solvent evaporation the residue was purified by column chromatography with EtOAc/hexane (37%) as eluent, affording alcohol 17 (103 mg, 32%) as a colorless oil; Rf: 0.23 (30% EtOAc/Hexane). $^1$H-NMR (CDCl$_3$, δ): 6.36 (1H, d, J=11.3 Hz, H-6), 6.01 (1H, d, J=11.3 Hz, H-7), 5.44 (1H, s, H-19), 5.20 (1H, d, J=2.2 Hz, H-19), 4.74 (6H, m, CH$_2$-MOM), 4.22 (1H, d, J=6.2 Hz, H-1), 4.06 (1H, dt, J=7.7/3.5 Hz, H-2), 3.90 (1H, dd, J=6.3/2.9 Hz, H-3), 3.42 (6H, s, CH$_3$-MOM), 3.37 (3H, s, CH$_3$-MOM), 2.82 (1H, m), 2.61 (1H, dd, J=13.7/8.2 Hz), 2.43 (1H, dd, J=13.6/4.1 Hz), 2.00 (2H, m), 1.88 (1H, dt, J=9.9/5.2 Hz), 1.68 (8H, m), 1.45 (6H, m), 1.22 (6H, s, CH$_3$-26/27), 1.05 (1H, m), 0.93 (3H, d, J=6.2 Hz, CH$_3$-21), 0.52 (3H, s, CH$_3$-18) ppm. $^{13}$C-NMR (CDCl$_3$, δ): 143.1 (C-10), 141.6 (C-8), 132.5 (C-5), 124.3 (CH-6), 117.1 (CH-7), 113.0 (CH$_2$-19), 95.9 (CH$_2$-MOM), 94.8 (CH$_2$-MOM), 91.0 (CH$_2$-MOM), 79.6 (CH-2), 76.4 (C-25), 75.7 (CH-1), 73.2 (CH-3), 56.5 (CH), 56.3 (CH), 55.7 (CH$_3$-MOM), 55.7 (CH$_3$-MOM), 55.1 (CH$_3$-MOM), 45.9 (C-13), 42.2 (CH$_2$), 40.5 (CH$_2$), 38.0 (CH$_2$), 36.4 (CH$_2$), 36.1 (CH-20), 29.1 (CH$_2$), 27.7 (CH$_2$), 26.5 (CH$_3$-26/27), 26.4 (CH$_3$-26/27), 23.6 (CH$_2$), 22.2 (CH$_2$), 20.5 (CH$_2$), 18.8 (CH$_3$-21), 11.9 (CH$_3$-18) ppm.

Synthesis of 3-(((1R,2R,6R,Z)-2,6-bis(methoxymethoxy)-4-(2-((1R,3aS,7aR,E)-1-((R)-6-(methoxymethoxy)-6-methylheptan-2-yl)-7a-methyl-octahydro-4H-inden-4-ylidene)ethylidene)-3-methylenecyclohexyl)oxy)propan-1-ol (18)

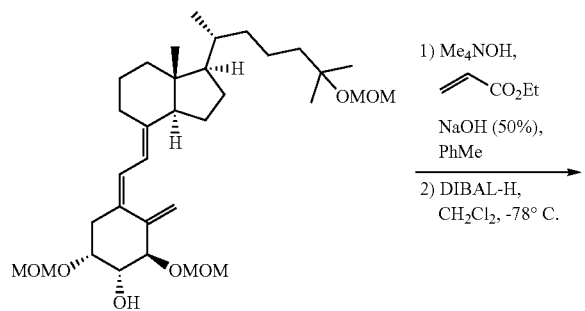

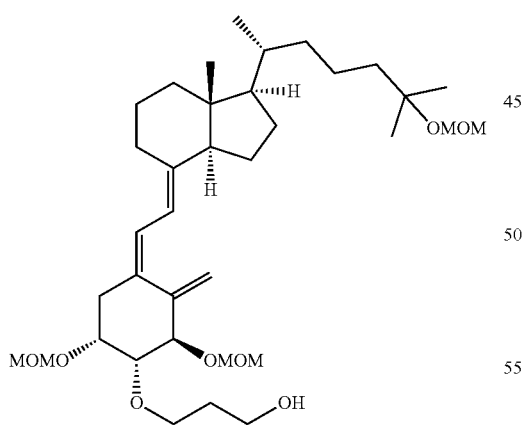

A mixture of alcohol 17 (97 mg, 0.17 mmol), ethyl acrylate (0.37 mL, 3.43 mmol), Me$_4$NOH (25% in H$_2$O, 20 μL) and NaOH (50% in H$_2$O, 1 mL) in PhMe (2.5 mL) was stirred vigorously at rt for 27 h. After that time, H$_2$O (3 mL) was added and the product was extracted with CH$_2$Cl$_2$ (3×10 mL). The combined organic phases were dried, filtered and evaporated to give a residue. To a solution of the previous residue in CH$_2$Cl$_2$ (1 mL) at -78° C. was added a solution of DIBAL-H 1.0 M in hexane (0.15 mL, 0.15 mmol) and the mixture was stirred for 6 h. After that time CH$_2$Cl$_2$ (3 mL) and a saturated solution of NH$_4$Cl (0.3 mL) were added. Then, Na$_2$SO$_4$ and silica gel were added and the mixture stirred for 20 min. The solution was concentrated to afford a residue which was chromatographed on silica gel using EtOAc/Hexane (60%) as eluent, affording alcohol 18 (25 mg, 23%) as a colorless oil; Rf: 0.12 (30% EtOAc/Hexane). $^1$H-NMR (CDCl$_3$, δ): 6.37 (1H, d, J=11.3 Hz, H-6), 6.02 (1H, d, J=11.2 Hz, H-7), 5.37 (1H, s, H-19), 5.22 (1H, s, H-19), 4.73 (2H, m, CH$_2$-MOM), 4.71 (4H, s, CH$_2$-MOM), 4.57 (1H, d, J=9.2 Hz, H-1), 4.29 (1H, d, J=3.5 Hz, H-3), 3.95 (2H, m, CH$_2$-3'), 3.80 (2H, m, CH$_2$-1'), 3.45 (1H, d, J=9.1 Hz, H-2), 3.43 (3H, s, CH$_3$-MOM), 3.40 (3H, s, CH$_3$-MOM), 3.39 (3H, s, CH$_3$-MOM), 3.03 (1H, d, J=12.0 Hz), 2.82 (1H, dd, J=14.7/4.0 Hz), 2.63 (1H, d, J=14.3 Hz), 2.00 (2H, m), 1.85 (3H, m), 1.70 (4H, m), 1.41 (6H, m), 1.27 (4H, m), 1.24 (6H, s, CH$_3$-26/27), 0.93 (3H, d, J=6.3 Hz, CH$_3$-21), 0.87 (m, 1H), 0.54 (3H, s, CH$_3$-18) ppm. $^{13}$C-NMR (CDCl$_3$, δ): 143.1 (C-10), 141.2 (C-8), 132.4 (C-5), 124.5 (CH-6), 118.9 (CH$_2$-19), 117.0 (CH-7), 95.5 (CH$_2$-MOM), 93.9 (CH$_2$-MOM), 91.0 (CH$_2$-MOM), 80.5 (CH-2), 77.2 (CH-1), 76.4 (C-25), 74.2 (CH-3), 70.4 (CH$_2$-1'), 62.1 (CH$_2$-3'), 56.5 (CH), 56.3 (CH), 55.7 (CH$_3$-MOM), 55.6 (CH$_3$-MOM), 55.1 (CH$_2$-MOM), 45.9 (C-13), 42.2 (CH$_2$), 40.5 (CH$_2$), 38.0 (CH$_2$), 36.4 (CH$_2$), 36.1 (CH-20), 32.0 (CH$_2$-2'), 29.0 (CH$_2$), 27.7 (CH$_2$), 26.5 (CH$_3$-26/27), 26.4 (CH$_3$-26/27), 23.5 (CH$_2$), 22.2 (CH$_2$), 20.5 (CH$_2$), 18.8 (CH$_3$-21), 14.2 (CH$_3$-18) ppm.

Synthesis of (R)-6-((1R,3aS,7aR,E)-4-((Z)-2-((3R,4R,5R)-3,5-bis(methoxymethoxy)-4-(3-(methoxymethoxy)propoxy)-2-methylenecyclohexylidene)ethylidene)-7a-methyloctahydro-1H-inden-1-yl)-2-methylheptan-2-ol (20)

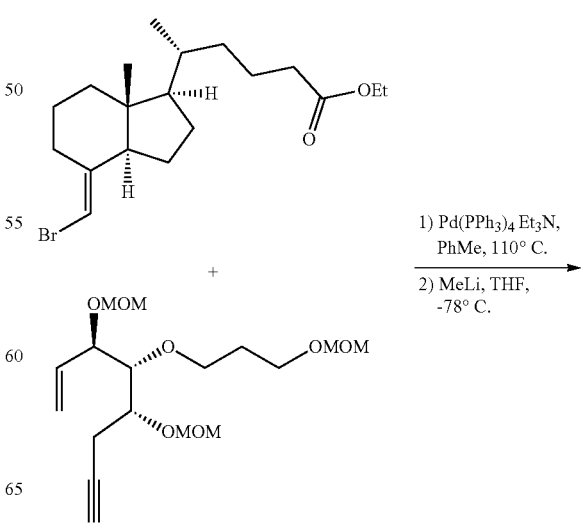

-continued

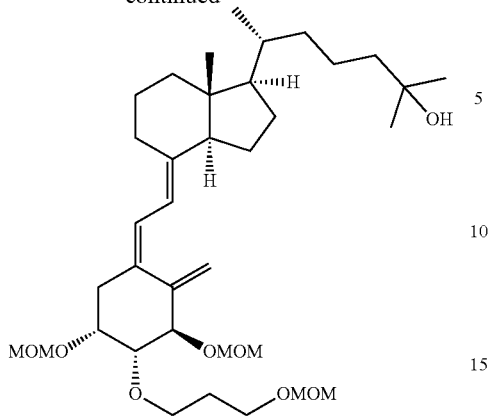

The enyne 15 (47 mg, 0.13 mmol) and vinyl bromide 19 (95 mg, 0.25 mmol) were dissolved in Et$_3$N/PhMe (1:1, 4 mL), and Pd(PPh$_3$)$_4$ was added in catalytic amount. The resulting yellow solution was stirred at 110° C. for 2 h. The reaction mixture was quenched with Et$_2$O (5 mL) and the solvent evaporated to afford a residue. To a solution of the previous residue in THF (3 mL) at −78° C. was added a solution of MeLi·LiBr 1.6 M in Et$_2$O (0.17 mL, 0.27 mmol) and the mixture was stirred for 3 h. H$_2$O (5 mL) was added and the product extracted with CH$_2$Cl$_2$ (3×10 mL). The combined organic phases were dried, filtered and evaporated to give a residue which was chromatographed on silica gel using EtOAc/Hexane (35%) as eluent, affording alcohol 20 (39 mg, 47%) as a colorless liquid; Rf: 0.43 (50% EtOAc/Hexane).

The invention claimed is:

1. A process for preparing a compound of formula (I)

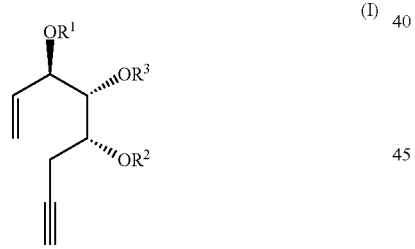

or a solvate thereof wherein
 $R^1$, $R^2$ and $R^3$ represent independently a hydroxyl protecting group, wherein $R^3$ is orthogonal to $R^1$ and $R^2$,
which comprises:
(a) oxidative cleavage of the double bond of a compound of formula (II) or a solvate thereof

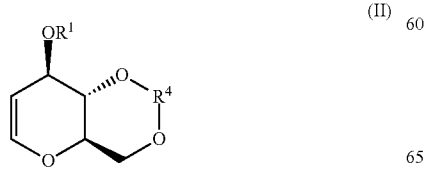

wherein $R^4$ is a diol protecting group which is orthogonal to $R^1$; to provide a compound of formula (III) or a solvate thereof

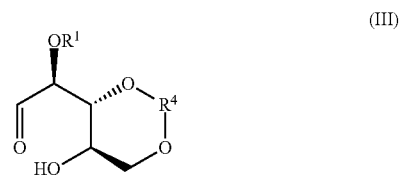

(b) vinylation of the aldehyde of a compound of formula (III), or a solvate thereof, to provide a compound of formula (IV) or a solvate thereof

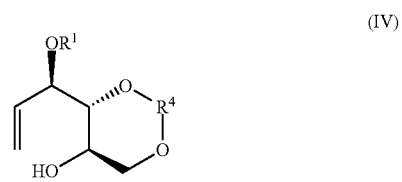

(c) protection of the hydroxyl group of a compound of formula (IV), or a solvate thereof, to provide a compound of formula (V) or a solvate thereof

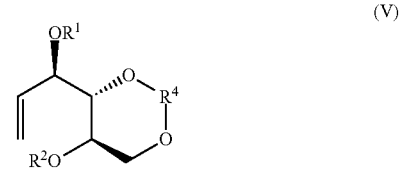

(d) cleavage of the diol protecting group of a compound of formula (V), or a solvate thereof, to provide a compound of formula (VI) or a solvate thereof

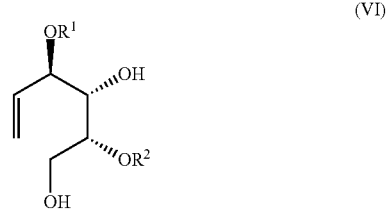

(e) conversion of the primary hydroxyl group into the homolog aldehyde and protection of the secondary hydroxyl of a compound of formula (VI), or a solvate thereof, to provide a compound of formula (VII) or a solvate thereof

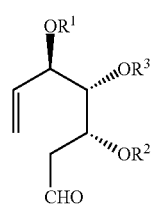
(VII)

and
(f) Corey-Fuchs reaction of a compound of formula (VII), or a solvate thereof, to provide a compound of formula (I) or a solvate thereof.

2. The process according to claim 1, wherein step (a) is carried out by treating a compound of formula (II), or a solvate thereof, with ozone followed by cleavage of the resulting ozonide.

3. The process according to claim 1, wherein step (b) is carried out by reacting a compound of formula (III), or a solvate thereof, with a compound of formula (XVIII), (XIX) or (XX)

$$X^- \;\; (R')_3\overset{+}{P}\diagdown$$
(XVIII)

$$\underset{(R''O)_2P}{\overset{O}{\|}}\diagdown$$
(XIX)

$$\underset{(R')_2P}{\overset{O}{\|}}\diagdown$$
(XX)

wherein
X is halogen;
each R' is selected from $C_6$-$C_{10}$ aryl; and
each R" is selected from $C_1$-$C_6$ alkyl and ($C_6$-$C_{10}$)aryl($C_1$-$C_6$)alkyl,
in the presence of a base.

4. The process according to claim 1, wherein step (e) comprises conversion of the primary hydroxyl group into the homolog nitrile, and optionally protection of the secondary hydroxyl group, to provide a compound of formula (XVI) or a solvate thereof

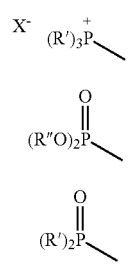
(XVI)

wherein
$R^1$ and $R^2$ represent independently a hydroxyl protecting group, and
$R^7$ is selected from hydrogen and a hydroxyl protecting group, provided that when $R^7$ is a hydroxyl protecting group it is orthogonal to $R^1$ and $R^2$;
and reduction of the nitrile group of a compound of formula (XVI), or a solvate thereof, and optionally protection of the secondary hydroxyl group to provide aldehyde (VII), or a solvate thereof.

5. The process according to claim 4, wherein step (e) comprises conversion of the primary hydroxyl group of a compound of formula (VI), or a solvate thereof, into a leaving group to provide a compound of formula (XVII) or a solvate thereof

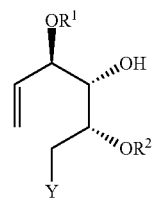
(XVII)

wherein Y is a leaving group;
conversion of the leaving group into nitrile, reduction of the nitrile group, and protection of the secondary hydroxyl group before conversion of the leaving group into nitrile or before reduction of the nitrile or after reduction of the nitrile group to provide aldehyde (VII), or a solvate thereof.

6. The process according to claim 4, wherein reduction of the nitrile group to aldehyde is carried out in the presence of a metal hydride.

7. The process according to claim 1, wherein step (f) comprises treating a compound of formula (VII), or a salt or solvate thereof, with $CBr_4$ in the presence of $PPh_3$, followed by treatment with a base.

8. The process according to claim 1, which comprises converting the compound of formula (I), or a solvate thereof, into Eldecalcitol, or a salt or solvate thereof.

9. The process according to claim 1, which further comprises:
(g) reaction of a compound of formula (I)

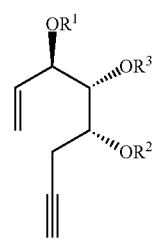
(I)

or a solvate thereof wherein
$R^1$, $R^2$ and $R^3$ represent independently a hydroxyl protecting group, wherein $R^3$ is orthogonal to $R^1$ and $R^2$;

with a compound of formula (IX) or with a compound of formula (XXV), or a solvate thereof

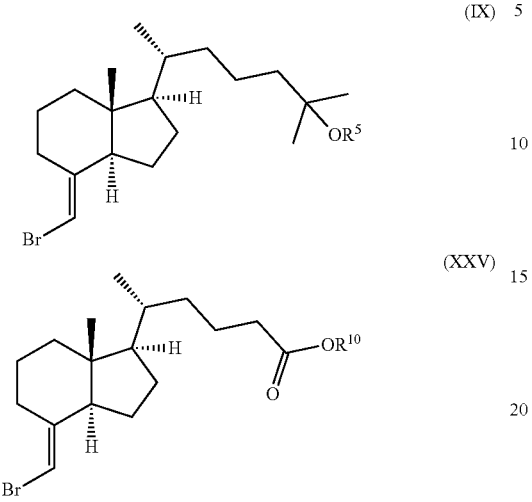

wherein
R$^5$ is selected from hydrogen and hydroxyl protecting group,
R$^{10}$ is selected from C$_1$-C$_6$ alkyl, C$_6$-C$_{10}$ aryl and (C$_6$-C$_{10}$)aryl(C$_1$-C$_6$)alkyl, to provide a compound of formula (X) or a compound of formula (XXVI), respectively, or a solvate thereof

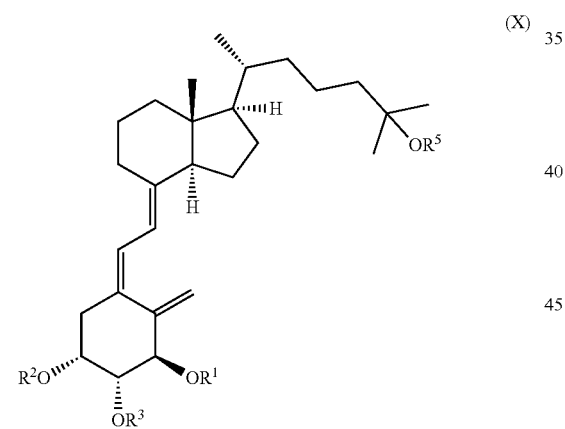

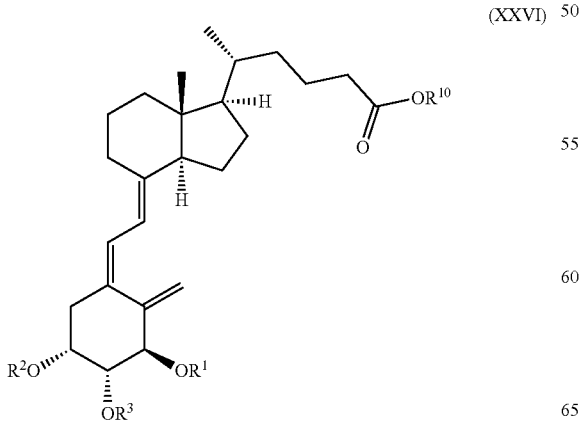

(h) when a compound of formula (XXVI) or a solvate thereof is obtained, reaction of a compound of formula (XXVI) with MeLi, and optionally protection of the resulting hydroxyl group, to provide a compound of formula (X) or a solvate thereof, (i) cleavage of the hydroxyl protecting group at position 2 in the compound of formula (X), or a solvate thereof, to provide a compound of formula (XI) or a solvate thereof

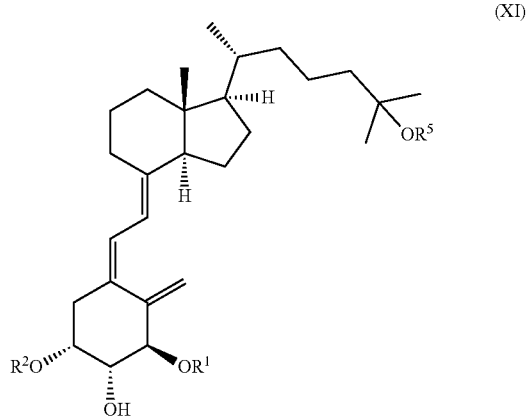

(j) reaction of a compound of formula (XI) with a compound of formula (XII) or with a compound of formula (XXII)

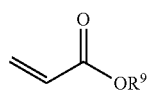

wherein
Z is a leaving group,
R$^6$ is selected from hydrogen and hydroxyl protecting group, and
R$^9$ is selected from C$_1$-C$_6$ alkyl, C$_6$-C$_{10}$ aryl and (C$_6$-C$_{10}$)aryl(C$_1$-C$_6$)alkyl, to provide a compound of formula (XIII), or a compound of formula (XXIII), respectively, or a solvate thereof (XIII)

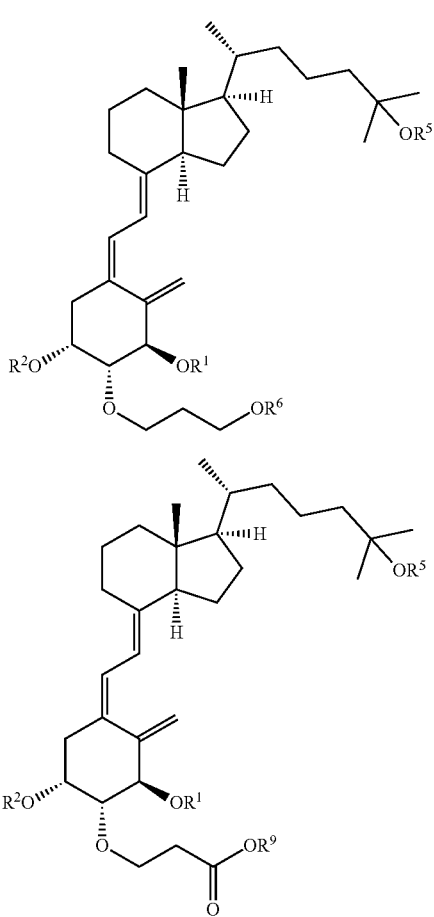

(XXIII)

(k) when a compound of formula (XXIII) or a solvate thereof is obtained, reduction of the ester group of a compound of formula (XXIII), or a solvate thereof, to provide a compound of formula (XXIV) or a solvate thereof (XXIV)

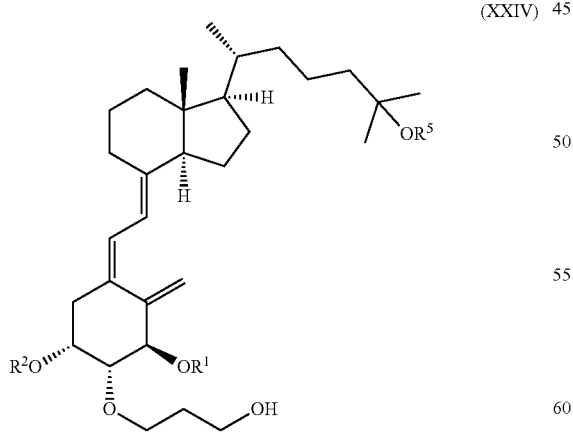

and
(l) cleavage of the hydroxyl protecting groups in the compound of formula (XIII) or (XXIV), or a solvate thereof, to provide Eldecalcitol, or a salt or solvate thereof.

10. The process according to claim 1, which further comprises:

(g') cleavage of the silyl protecting group in a compound of formula (I), or a solvate thereof, to provide a compound of formula (XIV)

(XIV)

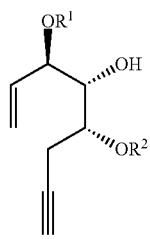

or a solvate thereof wherein $R^1$ and $R^2$ represent independently a hydroxyl protecting group;

(h') reaction of a compound of formula (XIV), or a solvate thereof, with a compound of formula (XII)

(XII)

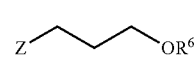

wherein

Z is a leaving group, and $R^6$ is selected from hydrogen and hydroxyl protecting group, to provide a compound of formula (XV) or a solvate thereof (XV)

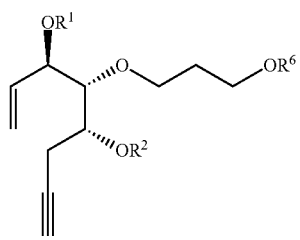

(i') reaction of a compound of formula (XV), or a solvate thereof, with a compound of formula (IX) or with a compound of formula (XXV), or a solvate thereof (IX)

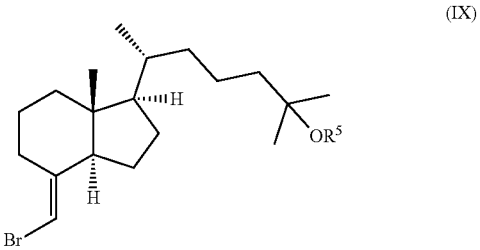

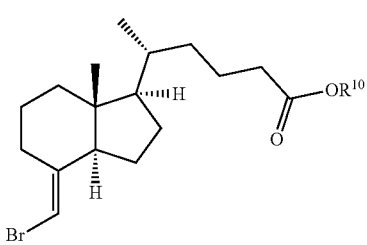

(XXV)

wherein
R[5] is selected from hydrogen and hydroxyl protecting group,
R[10] is selected from $C_1$-$C_6$ alkyl, $C_6$-$C_{10}$ aryl and ($C_6$-$C_{10}$)aryl($C_1$-$C_6$)alkyl, to provide a compound of formula (XIII) or a compound of formula (XXVII), respectively, or a solvate thereof (XIII)

(XXVII)

(j') when a compound of formula (XXVII) or a solvate thereof is obtained, reaction of a compound of formula (XXVII) with MeLi, and optionally protection of the resulting hydroxyl group, to provide a compound of formula (XIII) or a solvate thereof, (k') cleavage of the hydroxyl protecting groups in the compound of formula (XIII), or a solvate thereof, to provide Eldecalcitol, or a salt or solvate thereof.

11. A process for the preparation of Eldecalcitol, or a salt or solvate thereof, which comprises:

(A) reaction of a compound of formula (I)

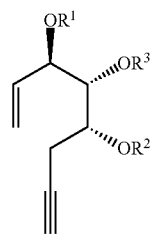

(I)

or a solvate thereof wherein
R[1], R[2] and R[3] represent independently a hydroxyl protecting group, wherein R[3] is orthogonal to R[1] and R[2];

with a compound of formula (IX) or with a compound of formula (XXV), or a solvate thereof (IX)

(XXV)

wherein
R⁵ is selected from hydrogen and hydroxyl protecting group,
R¹⁰ is selected from $C_1$-$C_6$ alkyl, $C_6$-$C_{10}$ aryl and ($C_6$-$C_{10}$oaryl($C_1$-$C_6$)alkyl, to provide a compound of formula (X) or a compound of formula (XXVI), respectively, or a solvate thereof

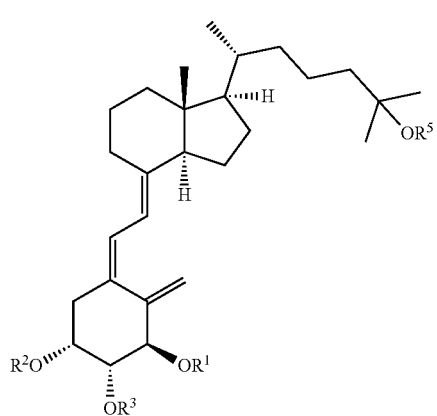

(X)

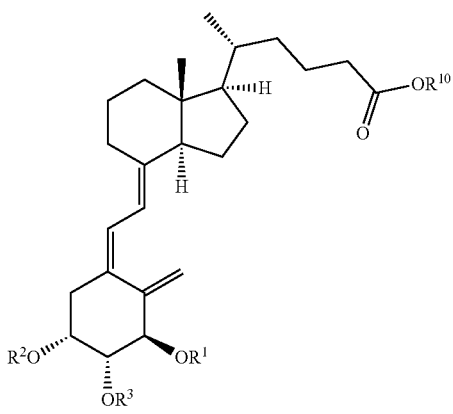

(XXVI)

(B) when a compound of formula (XXVI) or a solvate thereof is obtained, reaction of a compound of formula (XXVI) with MeLi, and optionally protection of the resulting hydroxyl group, to provide a compound of formula (X) or a solvate thereof, (C) cleavage of the hydroxyl protecting group at position 2 in the compound of formula (X), or a solvate thereof, to provide a compound of formula (XI) or a solvate thereof

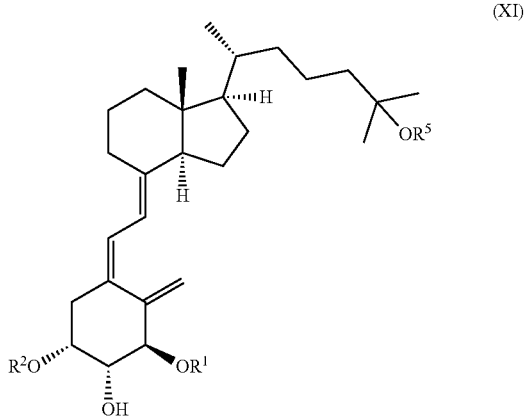

(XI)

(D) reaction of a compound of formula (XI) with a compound of formula (XII) or with a compound of formula (XXII)

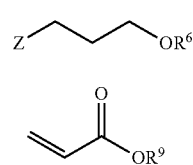

(XII)

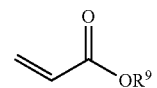

(XXII)

wherein
Z is a leaving group,
R⁶ is selected from hydrogen and hydroxyl protecting group, and
R⁹ is selected from $C_1$-$C_6$ alkyl, $C_6$-$C_{10}$ aryl and ($C_6$-$C_{10}$)aryl($C_1$-$C_6$)alkyl, to provide a compound of formula (XIII), or a compound of formula (XXIII), respectively, or a solvate thereof

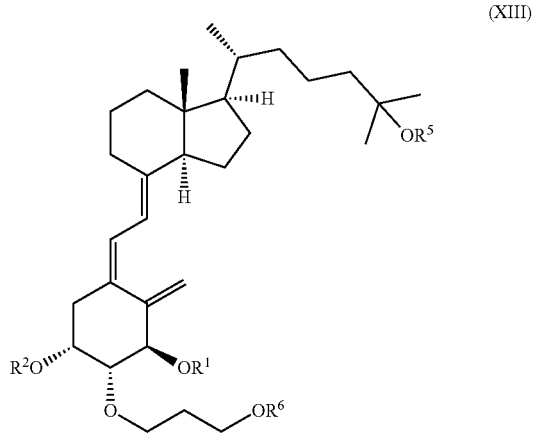

(XIII)

(XXIII)

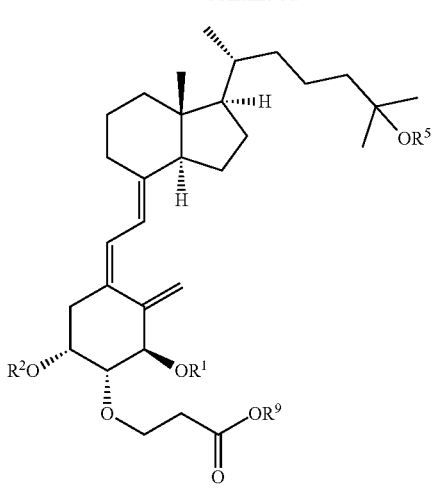

(E) when a compound of formula (XXIII) or a solvate thereof is obtained, reduction of the ester group of a compound of formula (XXIII), or a solvate thereof, to provide a compound of formula (XXIV) or a solvate thereof (XXIV)

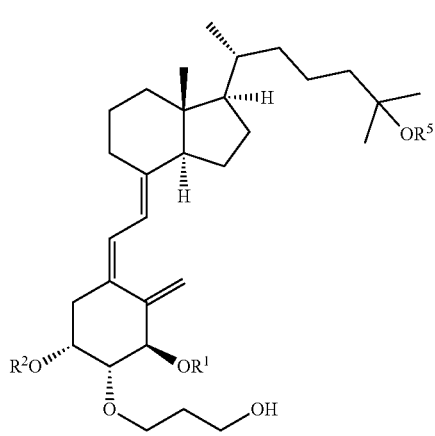

and
(F) cleavage of the hydroxyl protecting groups in the compound of formula (XIII), or in the compound of formula (XXIV), or a solvate thereof, to provide Eldecalcitol, or a salt or solvate thereof.

12. A compound selected from:
a compound of formula (I')

(I')

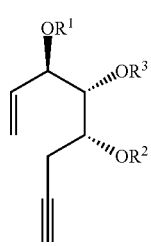

or a solvate thereof wherein
$R^1$ and $R^2$ represent independently a group selected from:
  $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
  —$CH_2$—$OR^a$, wherein $R^a$ is selected from $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
  —$COR^b$, wherein $R^b$ is selected from $C_1$-$C_6$ alkyl, $C_6$-$C_{10}$ aryl and ($C_6$-$C_{10}$)aryl($C_1$-$C_6$)alkyl, and
  —$COOR^c$, wherein $R^c$ is selected from $C_1$-$C_6$ alkyl, $C_6$-$C_{10}$ aryl and ($C_6$-$C_{10}$)aryl($C_1$-$C_6$)alkyl; and
$R^3$ is a hydroxyl protecting group orthogonal to $R^1$ and $R^2$; or
a compound of formula (XI)

(XI)

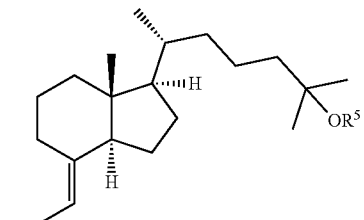

or a solvate thereof wherein
$R^1$ and $R^2$ represent independently a hydroxyl protecting group; and
$R^5$ is selected from hydrogen and hydroxyl protecting group; or
a compound of formula (XXIII)

(XXIII)

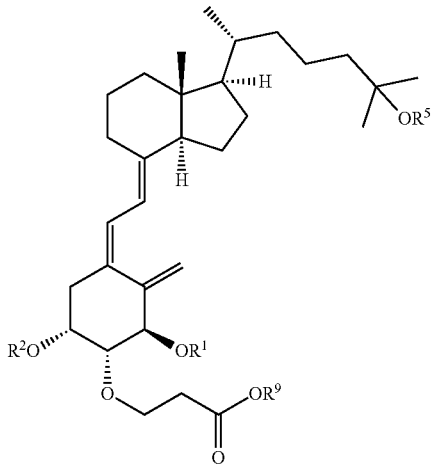

or a solvate thereof wherein
$R^1$ and $R^2$ represent independently a hydroxyl protecting group;
$R^5$ is selected from hydrogen and hydroxyl protecting group, and $R^9$ is selected from $C_1$-$C_6$ alkyl, $C_6$-$C_{10}$ aryl and ($C_6$-$C_{10}$)aryl($C_1$-$C_6$)alkyl.

13. The process according to claim 1, wherein $R^1$ and $R^2$ are independently selected from:
   $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
   —$CH_2$—$OR^a$, wherein $R^a$ is selected from $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
   —$COR^b$, wherein $R^b$ is selected from $C_1$-$C_6$ alkyl, $C_6$-$C_{10}$ aryl and ($C_6$-$C_{10}$)aryl($C_1$-$C_6$)alkyl, and
   —$COOR^c$, wherein $R^c$ is selected from $C_1$-$C_6$ alkyl, $C_6$-$C_{10}$ aryl and ($C_6$-$C_{10}$)aryl($C_1$-$C_6$)alkyl.

14. The process according to claim 1, wherein $R^3$ represents —$SiR^8{}_3$, wherein each $R^8$ is independently selected from $C_1$-$C_6$ alkyl, $C_3$-$C_7$ cycloalkyl, $C_6$-$C_{10}$ aryl, ($C_6$-$C_{10}$)aryl($C_1$-$C_6$)alkyl, $C_1$-$C_6$ alkoxy and halogen.

15. The process according to claim 2, wherein cleavage of the ozonide is carried out by treatment with tri($C_1$-$C_6$ alkyl)phosphines, tri($C_6$-$C_{10}$ aryl)phosphines, di($C_1$-$C_6$ alkyl)sulfides, thiourea or Zn/acetic acid.

16. The process according to claim 3, wherein the base is selected from organolithium bases, alkali metal hydrides and alkali metal alcoholates.

17. The process according to claim 6, wherein the metal hydride is selected from DIBAL, $LiAlH_4$, $LiAlH(OEt)_3$, $LiAlH(OMe)_3$, $LiAlH(OtBu)_3$ and $NaBH_4$.

18. The process according to claim 7, wherein the base is selected from nBuLi, tBuLi, sBuLi, MeLi, PhLi, HMDSLi and LDA.

19. The compound according to claim 12, wherein $R^1$ and $R^2$ are independently selected from:
   $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
   —$CH_2$—$OR^a$, wherein $R^a$ is selected from $C_1$-$C_6$ alkyl, $C_6$-$C_{10}$ aryl, ($C_6$-$C_{10}$)aryl($C_1$-$C_6$)alkyl and ($C_1$-$C_6$)alkoxy($C_1$-$C_6$)alkyl,
   —$COR^b$, wherein $R^b$ is selected from $C_1$-$C_6$ alkyl, $C_6$-$C_{10}$ aryl and ($C_6$-$C_{10}$)aryl($C_1$-$C_6$)alkyl, and
   —$COOR^c$, wherein $R^c$ is selected from $C_1$-$C_6$ alkyl, $C_6$-$C_{10}$ aryl and ($C_6$-$C_{10}$)aryl($C_1$-$C_6$)alkyl.

20. The compound according to claim 12, wherein $R^3$ represents —$SiR^8{}_3$, wherein each $R^8$ is independently selected from $C_1$-$C_6$ alkyl, $C_3$-$C_7$ cycloalkyl, $C_6$-$C_{10}$ aryl, ($C_6$-$C_{10}$)aryl($C_1$-$C_6$)alkyl, $C_1$-$C_6$ alkoxy and halogen.

\* \* \* \* \*